(12) United States Patent
Hashimoto et al.

(10) Patent No.: US 10,111,456 B2
(45) Date of Patent: Oct. 30, 2018

(54) METHODS AND COMPOSITIONS FOR IDENTIFYING NBB1 MUTATIONS

(71) Applicant: 22nd Century Limited, LLC, Clarence, NY (US)

(72) Inventors: Takashi Hashimoto, Ikoma (JP); Akira Kato, Nara (JP)

(73) Assignee: 22nd Century Limited, LLC, Williamsville, NY (US)

( * ) Notice: Subject to any disclaimer, the term of this patent is extended or adjusted under 35 U.S.C. 154(b) by 0 days.

(21) Appl. No.: 15/422,460

(22) Filed: Feb. 1, 2017

(65) Prior Publication Data

US 2017/0166913 A1 Jun. 15, 2017

Related U.S. Application Data

(60) Division of application No. 14/685,361, filed on Apr. 13, 2015, now Pat. No. 9,834,780, which is a division of application No. 13/082,953, filed on Apr. 8, 2011, now Pat. No. 9,029,656, which is a continuation of application No. 11/579,661, filed as application No. PCT/IB2006/001741 on Feb. 28, 2006, now Pat. No. 8,791,329.

(60) Provisional application No. 60/656,536, filed on Feb. 28, 2005.

(51) Int. Cl.
| | |
|---|---|
| *C12Q 1/6811* | (2018.01) |
| *A24B 15/20* | (2006.01) |
| *A24B 13/02* | (2006.01) |
| *A24B 15/24* | (2006.01) |
| *A24B 15/18* | (2006.01) |
| *C07K 14/415* | (2006.01) |
| *C12N 15/82* | (2006.01) |
| *A24B 13/00* | (2006.01) |
| *A24D 1/00* | (2006.01) |

(52) U.S. Cl.
CPC .............. *A24B 15/18* (2013.01); *A24B 13/00* (2013.01); *A24B 13/02* (2013.01); *A24B 15/20* (2013.01); *A24B 15/243* (2013.01); *A24D 1/00* (2013.01); *C07K 14/415* (2013.01); *C12N 15/8218* (2013.01); *C12N 15/8243* (2013.01); *A23V 2002/00* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,407,956 A | 10/1983 | Howell | |
| 5,459,252 A | 10/1995 | Conkling et al. | |
| 5,466,785 A | 11/1995 | De Framond | |
| 5,633,363 A | 5/1997 | Colbert et al. | |
| 5,803,081 A | 9/1998 | O'Donnell et al. | |
| 5,837,848 A | 11/1998 | Ely et al. | |
| 5,837,876 A | 11/1998 | Conkling et al. | |
| 5,852,041 A | 12/1998 | Cosford et al. | |
| 5,917,127 A | 6/1999 | Willmitzer | |
| 6,018,099 A | 1/2000 | De Framond | |
| 6,135,121 A | 10/2000 | Williams | |
| 6,423,520 B1 | 7/2002 | Conkling et al. | |
| 6,586,661 B1 | 7/2003 | Conkling et al. | |
| 6,805,134 B2 | 10/2004 | Peele | |
| 6,895,974 B2 | 5/2005 | Peele | |
| 6,907,887 B2 * | 6/2005 | Conkling ............... | A24B 15/10 131/270 |
| 6,959,712 B2 | 11/2005 | Bereman et al. | |
| 8,097,710 B2 | 1/2012 | Baulcombe et al. | |
| 8,791,329 B2 | 7/2014 | Hashimoto | |
| 9,834,780 B2 | 12/2017 | Hashimoto et al. | |
| 2003/0106105 A1 | 6/2003 | Hoffmann et al. | |
| 2003/0221213 A1 | 11/2003 | Rommens et al. | |
| 2004/0107455 A1 | 6/2004 | Rommens et al. | |
| 2004/0143874 A1 | 7/2004 | Moller et al. | |
| 2005/0010974 A1 | 1/2005 | Milligan et al. | |
| 2005/0018307 A1 | 1/2005 | Kamijima | |
| 2005/0034365 A1 | 2/2005 | Li et al. | |
| 2005/0072047 A1 | 4/2005 | Conkling et al. | |
| 2005/0097633 A1 | 5/2005 | Diehn et al. | |
| 2005/0223442 A1 | 10/2005 | Xu | |
| 2006/0041949 A1 | 2/2006 | Xu et al. | |
| 2006/0191036 A1 | 8/2006 | Conkling et al. | |
| 2008/0120737 A1 | 5/2008 | Hashimoto | |

FOREIGN PATENT DOCUMENTS

| | | |
|---|---|---|
| GB | 2 416 770 | 2/2006 |
| KR | 10200419301 | 3/2004 |
| WO | WO-98/56923 | 10/1998 |
| WO | WO-00/52168 | 9/2000 |
| WO | WO-01/59086 A2 | 8/2001 |
| WO | WO-02/38588 A2 | 5/2002 |
| WO | WO 02/066625 | 8/2002 |
| WO | WO-02/100199 A2 | 12/2002 |
| WO | WO-03/013226 A2 | 2/2003 |

(Continued)

OTHER PUBLICATIONS

Goossens et al, 2003, PNAS, 100:8595-8600.*
A. de la Peña et al., "Transgenic rye plants obtained by injecting DNA into young floral tillers", Nature, vol. 325, Jan. 15, 1987, pp. 274-276.
Advisory Action U.S. Appl. No. 11/579,661 dated Nov. 15, 2010.
Akama et al., "Efficient transformation of *Arabidopsis thaliana*: comparison of the efficiencies with various organs, plant ecotypes and Agrobacterium strains", Plant Cell Reports (1992) 12: 7-11.
Altschul et al., "Gapped BLAST and PSI-BLAST: a new generation of protein database search programs", Nucleic Acids Research, 1997, vol. 23, No. 17, pp. 3389-3402.

(Continued)

*Primary Examiner* — Jason Deveau Rosen
(74) *Attorney, Agent, or Firm* — Foley & Lardner LLP

(57) ABSTRACT

Two genes, A622 and NBB1, can be influenced to achieve a decrease of nicotinic alkaloid levels in plants. In particular, suppression of one or both of A622 and NBB1 may be used to decrease nicotine in tobacco plants.

10 Claims, 16 Drawing Sheets

Specification includes a Sequence Listing.

(56) References Cited

FOREIGN PATENT DOCUMENTS

| WO | WO-2004/076625 A2 | 9/2004 |
|---|---|---|
| WO | WO-2005/018307 A1 | 3/2005 |
| WO | WO-2005/116199 | 4/2005 |
| WO | WO-2005/103009 | 11/2005 |
| WO | WO-2005/107436 | 11/2005 |
| WO | WO-2005/111217 | 11/2005 |
| WO | WO-2005/113821 | 12/2005 |
| WO | WO-2005/121137 | 12/2005 |
| WO | WO-2006/008493 | 1/2006 |
| WO | WO-2006/010246 | 2/2006 |
| WO | WO-2006/015887 | 2/2006 |
| WO | WO-2006/025443 | 3/2006 |
| WO | WO-2006/091194 A1 | 8/2006 |

OTHER PUBLICATIONS

Archer et al., "Strategies for improving heterologous protein production from filamentous fungi", Antonie van Leeuwenhoek 65: 245-250, 1994.

Armitage et al., "Evaluation of a low to middle tar/medium nicotine cigarette designed to maintain nicotine delivery to the smoker", Psychopharmacology (1988) 96: 47-453.

Bacon et al., "Chemical Changes in Tobacco during Flue-Curing", Industrial and Engineering Chemistry, vol. 44, No. 2, pp. 292-296, Feb. 1952.

Beaucage et al., "Deoxynucleoside Phosphoramidites—A New Class of Key Intermediates for Deoxypolynucleotide Synthesis", Tetrahedron Letters, vol. 22, No. 20, pp. 1859-1862, 1981.

Bechtold et al., "In planta Agrobacterium mediated gene transfer by infiltration of adult *Arabidopsis thaliana* plants", C.R.Acad. Sci. Paris, Sciences de la vie/Life sciences, 1993:316, 1194-1199.

Beetham et al., A tool for functional plant genomics: Chimeric RNA/DNA oligonucleotides cause in vivo gene-specific mutations, Proc. Natl. Acad. Sci. USA, vol. 96, pp. 8774-8778, Jul. 1999.

Blank, C. et al., "Interaction of PD-L1 on tumor cells with PD-1 on tumor-specific T cells as a mechanism of immune evasion: implications for tumor immunotherapy", Cancer Immunol. Immunother. (2005) 54:307-314.

Broothaerts et al., "Gene transfer to plants by diverse species of bacteria", Nature, vol. 433, Feb. 10, 2005, pp. 629-633.

Bush et al., "Biosynthesis and metabolism of nicotine and related alkaloids", Nicotine and Related Alkaloids: Absorption Distribution Metabolism and Excretion, 1993, pp. 1-30.

Cane, K. et al., "Molecular analysis of alkaloid metabolism in *AABB* v. *aabb* genotype *Nicotiana tabacum* in response to wounding of aerial tissues and methyl jasmonate treatment of cultured roots", Functional Plant Biology, 2005, 32, 305-320.

Carter et al., "Tobacco Nectarin V Is a Flavin-Containing Berberine Bridge Enzyme-Like Protein with Glucose Oxidase Activity", Plant Physiology, Jan. 2004, vol. 134, pp. 460-469.

Chan et al., "*Ricinus communis* genomic scaffold scf_1106159295168, whole genome shotgun sequence", 2009, GenBank Accession No. EQ974633.

Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology 53: 87-105, 2003.

Clough et al., "Floral dip: a simplified method for Agrobacterium-mediated transformation of *Arabidopsis thaliana*", The Plant Journal (1998) 16(6), pp. 735-743.

Communication pursuant to Article 94(3) EPC EP Appln No: 06 848 676.0-2403 Dated Oct. 25, 2011.

Database EMBL Nicotiana benthamiana EST, Dec. 16, 2003, Buell, C.R. et al., "CK284001", XP002417091 retrieved from EBI Database accession No. CK284001 *Abstract.

Database EMBL Nicotiana tabacum mRNA for A622 Jul. 6, 1994, HIBI et al.: XP002429627 retrieved from EBI Database Accession No. D28505 *Abstract.

Database UniProt CPRD2 protein from *Vigna unguiculata* (cowpea) Jun. 1, 2001, S. Iuchi: "Q9AYM8_VIGUN", XP002417090, retrieved from EBI Database accession No. Q9AYM8 *Abstract.

Database UniProt Isoflavone reductase-like protein A622 Jul. 5, 2004, Shoji et al., XP002429628 retrieved from EBI Database Accession No. Q76LW3 *Abstract.

David et al., "Conservation of T-DNA in Plants Regenerated From Hairy Root Cultures", Bio/Technology, Jan. 1984, pp. 73-76.

Dittrich et al., "Molecular cloning, expression, and induction of berberine bridge enzyme, an enzyme essential to the formation of benzophenanthridine alkaloids in the response of plants to pathogenic attack", Proc. Natl. Acad. Sci., vol. 88, pp. 9969-9973, Nov. 1991.

Djordjevic et al., "Tobacco-Specific Nitrosamine Accumulation and Distribution in Flue-Cured Tobacco Alkaloid Isolines", J. Agric. Food Chem., 1989, 37, 752-756.

Dym, O. et al. "Sequence-structure analysis of FAD-containing proteins", Protein Science, 2001, vol. 10, pp. 1712-1728.

Fagenström, "Effects of a Nicotine-Enriched Cigarette on Nicotine Titration, Daily Cigarette Consuption, and Levels of Carbon Monoxide, Cotinine, and Nicotine", Psychopharmacology (1982) 77: 164-167.

Felpin et al., "Efficient Enantiomeric Synthesis of Pyrrolidine and Piperidine Alkaloids from Tobacco", J. Org. Chem. 2001, 66, 6305-6312.

Final Office Action in U.S. Appl. No. 11/579,661 dated Aug. 31, 2010.

Final Office Action U.S. Appl. No. 11/520,036 dated Jan. 28, 2011.

Goossens, A. et al. "A functional genomics approach toawrd the understanding of secondary metabolism in plant cells", PNAS, Jul. 8, 2003, vol. 100, No. 14, pp. 8595-8600.

Gori et al., "Analytical Cigarette Yields as Predictors of Smoke Bioavailability", Regulatory Toxicology and Pharmacology 5, 314-326 (1985).

Gossen et al., "Tight control of gene expression in mammalian cells by tetracycline-responsive promoters", Proc. Natl. Acad. Sci. USA, vol. 89, pp. 5547-5551, 1992.

Guo, Haiwei H. et al., "Protein tolerance to random amino acid change", Proc. Natl. Acad. Sci. USA (Jun. 22, 2004), vol. 101, No. 25, pp. 9205-9210.

Hakkinen, S. et al. "Functional characterisation of genes involved in pyridine alkaloid biosynthesis in tobacco", Phytochemistry, 2007, vol. 68, pp. 2773-2785.

Hamill, J. et al. "Over-expressing a yeast ornithine decarboxylase gene in transgenic roots of Nicotiana rustica can lead to enhanced nicotine accumulation", Plant Molecular Biology 15: 27-38, 1990.

Hashimoto, T. et al. "Intraspecific variability of the tandem repeats in Nicotiana putrescine N-methyltransferases", Plant Molecular Biology, 1998, vol. 37, pp. 25-37.

Hecht et al., "Tobacco-Specific Nitrosamines: Occurrence, Formation, Carcinogenicity, and Metabolism", Accounts of Chemical Research, 1979 American Chemical Society, vol. 12, pp. 92-98.

Hibi et al., "Putrescine N-Methyltransferase in Cultured Roots of Hyoscyamus albus", Plant Physiol. (1992), 100, 826-835.

Hibi, N. et al. "Gene Expression in Tobacco Low-Nicotine Mutants", The Plant Cell, May 1994, vol. 6, pp. 723-735.

Hoffmann et al., "Origin in Tobacco Smoke of N'-Nitrosonornicotine, a Tobacco-Specific Carcinogen: Brief Communication", J. Natl. Cancer Inst. vol. 58, No. 6, Jun. 1977, pp. 1841-1844.

Hoffmann et al., "The Changing Cigarette: Chemical Studies and Bioassays", Smoking and Tobacco Control Monograph No. 13, Chapter 5, Nov. 19, 2001, pp. 159-192.

Hoffmann et al., "Tobacco-Specific N-Nitrosamines and Areca-Derived N-Nitrosamines: Chemistry, Biochemistry, Carcinogenicity, and Relevance to Humans", Journal of Toxicology and Environmental Health, 41: 1-52, 1994.

Hsu et al., "Phloem Mobility of Xenobiotics VI. A Phloem-Mobile Pro-nematicide Based on Oxamyl Exhibiting Root-Specific Activation in Transgenic Tobacco", Pestic. Sci, 1995, 44, pp. 9-19.

Hwang et al., "An *Arabidopsis thaliana* root-specific kinase homolog is induced by dehydration, ABA, and NaCl", The Plant Journal (1995), 8(1), 37-43.

(56) References Cited

OTHER PUBLICATIONS

Kanegae et al., "Species-Dependent Expression of the Hyoscyamine 6β-Hydroxylase Gene in the Pericycle", Plant Physiol. (1994) 105: 483-490.
Katoh et al., "Analysis of expression sequence tags from Nicotiana sylvestris", Proc. Japan Acad. 79, No. 6, Ser. B (2003), pp. 151-154.
Klahre, U. et al. "High molecular weight RNAs and small interfering RNAs induce systemic posttranscriptional gene silencing in plants", PNAS, 2002, vol. 99, No. 18, pp. 11981-11986.
KR Application No. 10-2007-7022315, Notice of Non-Final Rejection dated Jul. 16, 2013.
Leegood, "16: Carbon Metabolism", Photosynthesis and Production in a Changing Environment a Field and Laboratory Manual, Edited by D.O. Hall et al.,(1993), pp. 247-267.
Legg, P. et al., "Inheritance of Per Cent Total Alkaloids in Nicotiana Tabacum L. II. Genetic Effects of Two Loci in Burley 21 X La Burley 21 Populations", Can. J. Genet. Cytol. 13: 287-291, 1971.
Lin, L. et al. "Steroleosin, a Sterol-Binding Dehydrogenase in Seed Oil Bodies", Plant Physiology, Apr. 2002, vol. 128, pp. 1200-1211.
Lörz et al., "Gene transfer to cereal cells mediated by protoplast transformation", Mol. Gen Genet (1985), 199: 178-182.
Matteucci et al., "Synthesis of Deoxyoligonucleotides on a Polymer Support", J. Am. Chem. Soc. 1981, 103, 3185-3191.
Mayfield et al., "Expression of human antibodies in eukaryotic micro-algae", Vaccine, 23, (2005), 1828-1832.
Miyagawa et al., "Evaluation of the Defense System in Chloroplasts to Photooxidative Stress Caused by Paraquat Using Transgenic Tobacco Plants Expressing Catalase from *Escherichia coli*", Plant Cell Physiol. 41(3): 311-320 (2000).
Miyagawa et al., "Overexpression of a cyanobacterial fructose-1,6-/sedoheptulose-1, 7-bisphosphatase in tobacco enhances photosynthesis and growth", Nature Biotechnolgoy, vol. 19, Oct. 2001, pp. 965-969.
Moyano et al., "Alkaloid production in Duboisia hybrid hairy root cultures overexpressing the pmt gene", Phytochemistry 59 (2002) 697-702.
Moyano et al., "Effect of pmt gene overexpression on tropane alkaloid production in transformed root cultures of Datura metal and Hyosyamus muticus", Jouranl fo Experimental Botany, vol. 54, No. 381, pp. 203-211, Jan. 2003.
Murillo et al., "Engineering photoassimilate partitioning in tobacco plants improves growth and productivity and provides pathogen resistance", The Plant Journal (2003) 36, 330-341.
Nagel et al., "Electroporation of binary Ti plasmid vector into Agrobacterium tumefaciens and Agrobacterium rhizogenes", FEMS Microbiology Letters, 67 (1990), 325-328.
New England BioLabs Catalog (1996/1997).
Non Final Office Action U.S. Appl. No. 11/579,661 dated Mar. 23, 2010.
Non-Final Office Action U.S. Appl. No. 11/579,661 dated Jul. 23, 2009.
Office Action in AU Appln No. 2012203977 dated Dec. 18, 2013.
Office Action in CA Appln No. 2,599,302 dated Jan. 9, 2014.
Office Action in CN Appln No. 200680010544X dated Sep. 16, 2010.
Office Action in CN Appln No. 201210252031.7 dated Oct. 24, 2013.
Office Action in U.S. Appl. No. 11/520,036 dated May 21, 2010.
Office Action in U.S. Appl. No. 11/520,036 dated Aug. 15, 2013.
Office Action in U.S. Appl. No. 11/579,661 dated Oct. 7, 2013.
Oksman-Caldentey et al., "Chapter 13: Regulation of Tropane Alkaloid Metabolism in Plants and Plant Cell Cultures", Metabolic Engineering of Plant Secondary Metabolism, Kluwar Academic Publishers, 2000, pp. 253-281.
Paszkowski et al., "Direct gene transfer to plants", The EMBO Journal, vol. 3, No. 12, pp. 2717-2722, 1984.
Pillsbury et al., "Tobacco Tar and Nicotine in Cigarette Smoke", Journal of the AOAC, vol. 52, No. 3, 1969, pp. 458-462.
Reed et al., "The A and B loci of Nicotiana tabacum have non-equivalent effects on the mRNA levels of four alkaloid biosynthetic genes", Plant Science 167 (2004) 1123-1130.
Restrepo et al., "Nuclear Transport of Plant Potyviral Proteins", The Plant Cell, vol. 2, 987-998, Oct. 1990.
Rhodes et al., "Genetically Transformed Maize Plants from Protoplasts", Science, vol. 240, Apr. 8, 1988, pp. 204-207.
Riechers et al., "Structure and expression of the gene family encoding putrescine N-methyltransferase in Nicotiana tabacum: new clues to the evolutionary origin of cultivated tobacco", Plant Molcular Biology 41: 387-401, 1999.
Rose, "The Role of Upper Airway Stimulation in Smoking", Nicotine Replacement: A Critical Evaluation, pp. 95-106, 1988.
Rothe et al., "Alkaloids in plants and root cultures of Atropa belladonna overexpressing putrescine N-methyltransferase", Journal of Experimental Botany, vol. 54, No. 390, pp. 2065-2070, Sep. 2003.
Rymerson, R.T. et al. "Immunogenicity of the capsid protein VP2 from porcine parvovirus expressed in low alkaloid transgenic tobacco", Molecular Breeding, May 4, 2003; 11(4):267-276.
Sagi et al., "Transient gene expression in electroporated banana (Musa spp., cv. 'Bluggoe', ABB group) protoplasts isolated from regenerable embryogenetic cell suspensions", Plant Cell Reports, (1994) 13: 262-266.
Saitoh et al., "The Alkaloid Contents of Sixty Nicotiana Species", Phytochemistry, vol. 24, No. 3, pp. 477-480, 1985.
Sambrook et al., "Chapter 7: Extraction, Purification, and Analysis of mRNA from Eukaryotic Cells", Molecular Cloning A Laboratory Manual vol. 1, Third Edition, 2001.
Sato, F. et al., "Metabolic engineering of plant alkaloid biosynthesis", PNAS, Jan. 2, 2001, vol. 98, No. 1, 367-372.
Shimamoto et al., "Fertile transgenic rice plants regenerated from transformed protoplasts", Nature, vol. 338, Mar. 16, 1989, pp. 274-276.
Shoji et al., "Ethylene Suppresses Jasmonate-Induced Gene Expression in Nicotine Bio-synthesis", Plant Cell Physiol. 41(9): 1072-1076, (2000).
Shoji et al., "Expression patterns of two tobacco isoflavone reductase-like genes and their possible roles in secondary metabolism in tobacco", Plant Molecular Biology 50: 427-440, 2002.
Shoji et al., "Jasmonate Induction of Putrescine N-Methyltransferase Genes in the Root of Nicotiana sylvestris", Plant Cell Physiol. 41(7): 831-839 (2000).
Sinclair et al., "Molecular characterization of puinolinate phosphoribosyltransferase (QPRTase) in Nicotiana", Plant Molecular Biology, 44: 603-617, 2000.
Sinclair, S. et al., "Analysis of wound-induced gene expression in Nicotiana species with contrasting alkaloid profiles", Functional Plant Biology, 2004, 31, 721-729.
Singer, "The Upside to Nicotine?", Technology Review: MIT's Magazine of Innovation, vol. 109, No. 3, Jul.-Aug. 2006.
Steppuhn et al., "Nicotine's Defensive Function in Nature", PLoS Biology, Aug. 2004, vol. 2, Issue 8, 1074-1080.
Stratton et al., "Clearing the Smoke Assessing the Science Base for Tobacco Harm Reduction", Committee to Assess the Science Base for Tobacco Harm Reduction, Board on Health Promotion and Disease Prevention, Institute of Medicine, 2001.
Tamoi et al., "Contribution of Fructose-1,6-bisphosphatase and Sedoheptulose-1,7-bisphosphatase to the Photosynthetic Rate and Carbon Flow in the Calvin Cycle in Transgenic Plants", Plant Cell Physiol. 47(3): 380-390 (2006).
Thomas, C. et al. "Size constraints for targeting post-transcriptional gene silencing and for RNA-directed methylation in Nicotiana benthamiana using a potato virus X vector", The Plant Journal, 2001, vol. 25, No. 4, pp. 417-425.
Thompson et al., "Characterization of the herbicide-resistance gene bar from Streptomyces hygroscopicus", The EMBO Journal, vol. 6, No. 9, pp. 2519-2523, 1987.
Tobacco: Production, Chemistry and Technology,—Breeding and Genetics,1999, CORESTA Blackwell Science Ltd., Edited by D. Layten Davis et al., 1999, pp. 45-46.

(56) References Cited

OTHER PUBLICATIONS

Trabattoni, D. et al., "B7-H1 is up-regulated in HIV infection and is a novel surrogate marker of disease progression", BLOOD, Apr. 1, 2003, vol. 101, No. 7, pp. 2514-2520.
Tso, "Production, Physiology, and Biochemistry of Tobacco Plant", 1990, IDEALS Inc.
UniProtKB Accession No. A7WPL6 (A7WPL6_TOBAC)—berberine bridge enzyme like protein—*Nicotiana tabacum* (Common tobacco), Oct. 23, 2007, Accessed Jul. 30, 2013.
Voelckel et al., "Anti-sense expression of putrescine N-methyltransferase confirms defensive role of nicotine in Nocotiana sylvestris against Manduca sexta", Chemoecology 11: 121-126 (2001).
Woodman et al., "The separate effects of tar and nicotine on the cigarette smoking manoeuvre", Eur J Respir Dis, (1987) 70, pp. 316-321.
Zhang et al., "Engineering tropane biosynthetic pathway in Hyosyamus niger hairy root cultures", PNAS, Apr. 2004, vol. 101, No. 17, pp. 6786-6791.
Zhu et al., "Targeted manipulation of maize genes in vivo using chimeric RNA/DNA oligonucleotides", Proc. Natl. Acad. Sci. USA, vol. 96, pp. 8768-8773, Jul. 1999.
Zoller et al., "Oligonucleotide-directed mutagenesis using M13-derived vectors: an efficient and general procedure for the production of point mutations in any fragment of DNA", Nucleic Acids Research, vol. 10, No. 20, 1982, pp. 6487-6500.
Non-Final Office Action issued in related U.S. Appl. No. 11/520,036, dated Jun. 8, 2015.
Office Action issued in related U.S. Appl. No. 11/520,036, dated Oct. 1, 2015.
Office Action issued in related Canadian Patent Application No. 2872521, dated Nov. 13, 2015.
Office Action issued in related U.S. Appl. No. 14/444,511, dated Jun. 15, 2016.
Office Action issued in related U.S. Appl. No. 14/444,511, dated Sep. 28, 2016.
Notice of Allowance issued in related U.S. Appl. No. 11/520,036, dated Sep. 6, 2016.
Office Action issued in related U.S. Appl. No. 14/687,910, dated Nov. 25, 2016.
Dewey et al., "Molecular Genetics of Alkaloid Biosynthesis in Nicotiana Tabacum," Phytochemistry 94, pp. 10-27 (2013).
Office Action issued in related U.S. Appl. No. 14/685,361, dated Jan. 19, 2017.
Office Action issued in related U.S. Appl. No. 14/444,511, dated Apr. 28, 2017.
Notice of Allowance issued in related U.S. Appl. No. 14/687,910, dated Mar. 31, 2017.
Notice of Allowance issued in related U.S. Appl. No. 14/685,361, dated Aug. 7, 2017.
Notice of Allowance issued in related U.S. Appl. No. 14/444,511, dated Aug. 23, 2017.
Supplemental Notice of Allowance issued in related U.S. Appl. No. 14/444,511, dated Sep. 14, 2017.
Supplemental Notice of Allowance issued in related U.S. Appl. No. 14/685,361, dated Oct. 4, 2017.
Non-Final Office Action issued in related U.S. Appl. No. 15/828,868, dated Jan. 30, 2018.
Non-Final Office Action issued in related U.S. Appl. No. 15/828,875, dated Jan. 30, 2018.
Non-Final Office Action issued in related U.S. Appl. No. 15/422,455, dated Feb. 22, 2018.
Office Action issued in co-pending U.S. Appl. No. 15/411,721, dated Apr. 10, 2018.
Weiner et al., "NADP+ Binding to Dehydrogenases," *Handbook of Proteins*, vol. 1, pp. 626-632 (2007).
Kajikawa et al., "Vacuole-Localized berberine bridge Enzyme-Like Proteins are Required for a Late Step of Nicotine Biosynthesis in tobacco," *Plant Physiology*, vol. 155, pp. 2010-2022 (2011).
Corrected Notice of Allowance issued in related U.S. Appl. No. 15/828,868, dated Jun. 27, 2018.
Corrected Notice of Allowance issued in related U.S. Appl. No. 15/828,875, dated Jun. 27, 2018.
Notice of Allowance issued in related U.S. Appl. No. 15/828,868, dated May 29, 2018.
Notice of Allowance issued in related U.S. Appl. No. 15/828,875, dated May 18, 2018.

\* cited by examiner

Preparation of plant RNAi binary vector

T-DNA region of pRNAi-A622

Expression of A622, PMT, and tubulin by RT-PCR (Figure 8A) and nicotine content (Figure 8B) in tobacco hairy root lines.

RNA blot analysis of NBB1 expression

Figure 10: Alignment of NBB1 with Eschscholzia californica berberine bridge enzyme (EcBBE)

T-DNA region of pHANNIBAL-NBB1 3'

Gene Expression in NBB1-silenced Hairy Roots. NBB1-silenced: N6, N19, N20, N29. Vector control: VC

SEQUENCE LISTING

<160> NUMBER OF SEQ ID NOS: 37

<210> SEQ ID NO 1
<211> LENGTH: 1179
<212> TYPE: DNA
<213> ORGANISM: Nicotiana tabacum

<400> SEQUENCE: 1

```
aaaaatccga tttaattcct agtttctagc ccctccacct taacccgaag ctactttttt      60
tcttccccta ggagtaaaat ggttgtatca gagaaaagca agatcttaat aattggaggc     120
acaggctaca taggaaaata cttggtggag acaagtgcaa aatctgggca tccaactttc     180
gctcttatca gagaaagcac actcaaaaac cccgagaaat caaaactcat cgacacattc     240
aagagttatg gggttacgct acttttggga gatatatcca atcaagagag cttactcaag     300
gcaatcaagc aagttgatgt ggtgatttcc actgtcggag acagcaatt tactgatcaa      360
gtgaacatca tcaaagcaat taagaagct ggaaatatca agagatttct tccttcagaa      420
tttggatttg atgtggatca tgctcgtgca attgaaccag ctgcatcact cttcgctcta     480
aaggtaagaa tcaggaggat gatagaggca gaaggaattc catacacata tgtaatctgc     540
aattggtttg cagatttctt cttgcccaac ttggggcagt tagaggccaa aacccctcct     600
agagacaaag ttgtcatttt tggcgatgga aatcccaaag caatatatgt gaaggaagaa     660
gacatagcga catacactat cgaagcagta gatgatccac ggacattgaa taagactctt     720
cacatgagac cacctgccaa tattctatcc ttcaacgaga tagtgtcctt gtgggaggac     780
aaaattggga agaccctcga gaagttatat ctatcagagg aagatattct ccagattgta     840
caagagggac ctctgccatt aaggactaat ttggccatat gccattcagt ttttgttaat     900
ggagattctg caaactttga ggttcagcct cctacaggtg tcgaagccac tgagctatat     960
ccaaaagtga aatacacaac cgtcgacgag ttctacaaca aatttgtcta gtttgtcgat    1020
atcaatctgc ggtgactcta tcaaacttgt tgtttctatg aatctattga gtgtaattgc    1080
aataattttc gcttcagtgc ttttgcaact gaaatgtact agctagttga acgctagcta    1140
aattctttac tgttgttttc tatttttcgt cttattcca                           1179
```

<210> SEQ ID NO 2
<211> LENGTH: 310
<212> TYPE: PRT
<213> ORGANISM: Nicotiana tabacum

<400> SEQUENCE: 2

```
Met Val Val Ser Glu Lys Ser Lys Ile Leu Ile Ile Gly Gly Thr Gly
  1               5                  10                  15

Tyr Ile Gly Lys Tyr Leu Val Glu Thr Ser Ala Lys Ser Gly His Pro
             20                  25                  30

Thr Phe Ala Leu Ile Arg Glu Ser Thr Leu Lys Asn Pro Glu Lys Ser
         35                  40                  45

Lys Leu Ile Asp Thr Phe Lys Ser Tyr Gly Val Thr Leu Leu Phe Gly
 50                  55                  60

Asp Ile Ser Asn Gln Glu Ser Leu Leu Lys Ala Ile Lys Gln Val Asp
 65                  70                  75                  80

Val Val Ile Ser Thr Val Gly Gly Gln Gln Phe Thr Asp Gln Val Asn
                 85                  90                  95

Ile Ile Lys Ala Ile Lys Glu Ala Gly Asn Ile Lys Arg Phe Leu Pro
            100                 105                 110
```

```
Ser Glu Phe Gly Phe Asp Val Asp His Ala Arg Ala Ile Glu Pro Ala
            115                 120                 125
Ala Ser Leu Phe Ala Leu Lys Val Arg Ile Arg Met Ile Glu Ala
        130                 135                 140
Glu Gly Ile Pro Tyr Thr Tyr Val Ile Cys Asn Trp Phe Ala Asp Phe
145                 150                 155                 160
Phe Leu Pro Asn Leu Gly Gln Leu Glu Ala Lys Thr Pro Pro Arg Asp
                165                 170                 175
Lys Val Val Ile Phe Gly Asp Gly Asn Pro Lys Ala Ile Tyr Val Lys
            180                 185                 190
Glu Glu Asp Ile Ala Thr Tyr Thr Ile Glu Ala Val Asp Asp Pro Arg
        195                 200                 205
Thr Leu Asn Lys Thr Leu His Met Arg Pro Pro Ala Asn Ile Leu Ser
210                 215                 220
Phe Asn Glu Ile Val Ser Leu Trp Glu Asp Lys Ile Gly Lys Thr Leu
225                 230                 235                 240
Glu Lys Leu Tyr Leu Ser Glu Glu Asp Ile Leu Gln Ile Val Gln Glu
                245                 250                 255
Gly Pro Leu Pro Leu Arg Thr Asn Leu Ala Ile Cys His Ser Val Phe
            260                 265                 270
Val Asn Gly Asp Ser Ala Asn Phe Glu Val Gln Pro Pro Thr Gly Val
        275                 280                 285
Glu Ala Thr Glu Leu Tyr Pro Lys Val Lys Tyr Thr Thr Val Asp Glu
290                 295                 300
Phe Tyr Asn Lys Phe Val
305                 310

<210> SEQ ID NO 3
<211> LENGTH: 1749
<212> TYPE: DNA
<213> ORGANISM: Nicotiana tabacum

<400> SEQUENCE: 3
acgcggggag aaatacatac aacatgtttc cgctcataat tctgatcagc ttttcacttg    60
cttccttgtc tgaaactgct actggagctg ttacaaatct ttcagcctgc ttaatcaacc   120
acaatgtcca taacttctct atttacccca caagtagaaa ttactttaac ttgctccact   180
tctcccttca aatcttcgc tttgctgcac ctttcatgcc gaaaccaacc ttcattatcc   240
taccaagcag taaggaggag ctcgtgagca ccattttttg ttgcagaaaa gcatcttatg   300
aaatcagagt aaggtgcggc ggacacagtt acgaaggaac ttcttacgtt ccttttgacg   360
cttctccatt cgtgatcgtt gacttgatga attagacga cgtttcagta gatttggatt   420
ctgaaacagc ttgggctcag gcggcgcaa caattggcca aatttattat gccattgcca   480
aggtaagtga cgttcatgca ttttcagcag gttcgggacc aacagtagga tctggaggtc   540
atatttcagg tggtggattt ggacttttat ctagaaaatt cggacttgct gctgataatg   600
tcgttgatgc tcttccttatt gatgctgatg gacggttatt agaccgaaaa gccatgggcg   660
aagacgtgtt tgggcaatc agaggtggcg gcggtggaaa ttggggcatt gtttatgcct   720
ggaaaattcg attactcaaa gtgcctaaaa tcgtaacaac ttgtatgatc tataggcctg   780
gatccaaaca atacgtggct caaatacttg agaaatggca atagttact ccaaatttgg   840
tcgatgattt tactctagga gtactgctga gacctgcaga tctacccgcg gatatgaaat   900
atggtaatac tactcctatt gaaatattc cccaattcaa tgcactttat ttgggtccaa   960
```

```
aaactgaagt tctttccata tcgaatgaga catttccgga gctaggcgtt aagaatgatg    1020
agtgcaagga atgacttgg gtagagtcag cacttttctt ctccgaatta gctgacgtta    1080
acgggaactc gactggtgat atctcccgtc tgaaagaacg ttacatggac ggaaaaggtt    1140
ttttcaaagg caaacggac tacgtgaaga agccagtttc aatggatggg atgctaacat    1200
ttcttgtgga actcgagaaa aacccgaagg gatatcttgt ctttgatcct tatggcggag    1260
ccatggacaa gattagtgat caagctattg cttccctca tagaaaaggt aaccttttcg    1320
cgattcagta tctagcacag tggaatgaag aggacgatta catgagcgac gtttacatgg    1380
agtggataag aggattttac aatacaatga cgcccttttgt ttcaagctcg ccaaggggag    1440
cttatatcaa ctacttggat atggatcttg gagtgaatat ggtcgacgac tacttattgc    1500
gaaatgctag tagcagtagt ccttcttcct ctgttgatgc tgtggagaga gctgagcgt    1560 ggggtgagat gtatttcttg cataactatg ataggttggt taaagctaag acacaaattg    1620
atccactaaa tgttttcga catgaacaga gtattcctcc tatgcttggt tcaacgcaag    1680
agcacaagta tagcagtgaa tgagatttaa aatgtactac cttgagagag attccgttgt    1740
tagttttcc                                                            1749
```

<210> SEQ ID NO 4
<211> LENGTH: 559
<212> TYPE: PRT
<213> ORGANISM: Nicotiana sylvestris

<400> SEQUENCE: 4

```
Met Phe Pro Leu Ile Ile Leu Ile Ser Phe Ser Leu Ala Ser Leu Ser
  1               5                  10                  15

Glu Thr Ala Thr Gly Ala Val Thr Asn Leu Ser Ala Cys Leu Ile Asn
             20                  25                  30

His Asn Val His Asn Phe Ser Ile Tyr Pro Thr Ser Arg Asn Tyr Phe
         35                  40                  45

Asn Leu Leu His Phe Ser Leu Gln Asn Leu Arg Phe Ala Ala Pro Phe
     50                  55                  60

Met Pro Lys Pro Thr Phe Ile Ile Leu Pro Ser Ser Lys Glu Glu Leu
 65                  70                  75                  80

Val Ser Thr Ile Phe Cys Cys Arg Lys Ala Ser Tyr Glu Ile Arg Val
                 85                  90                  95

Arg Cys Gly Gly His Ser Tyr Glu Gly Thr Ser Tyr Val Ser Phe Asp
            100                 105                 110

Ala Ser Pro Phe Val Ile Val Asp Leu Met Lys Leu Asp Asp Val Ser
        115                 120                 125

Val Asp Leu Asp Ser Glu Thr Ala Trp Ala Gln Gly Gly Ala Thr Ile
    130                 135                 140

Gly Gln Ile Tyr Tyr Ala Ile Ala Lys Val Ser Asp Val His Ala Phe
145                 150                 155                 160

Ser Ala Gly Ser Gly Pro Thr Val Gly Ser Gly His Ile Ser Gly
                165                 170                 175

Gly Gly Phe Gly Leu Leu Ser Arg Lys Phe Gly Leu Ala Ala Asp Asn
            180                 185                 190

Val Val Asp Ala Leu Leu Ile Asp Ala Asp Gly Arg Leu Leu Asp Arg
        195                 200                 205

Lys Ala Met Gly Glu Asp Val Phe Trp Ala Ile Arg Gly Gly Gly Gly
    210                 215                 220

Gly Asn Trp Gly Ile Val Tyr Ala Trp Lys Ile Arg Leu Leu Lys Val
```

```
                225                 230                 235                 240

Pro Lys Ile Val Thr Thr Cys Met Ile Tyr Arg Pro Gly Ser Lys Gln
                        245                 250                 255

Tyr Val Ala Gln Ile Leu Glu Lys Trp Gln Ile Val Thr Pro Asn Leu
                        260                 265                 270

Val Asp Asp Phe Thr Leu Gly Val Leu Leu Arg Pro Ala Asp Leu Pro
                        275                 280                 285

Ala Asp Met Lys Tyr Gly Asn Thr Thr Pro Ile Glu Ile Phe Pro Gln
                    290                 295                 300

Phe Asn Ala Leu Tyr Leu Gly Pro Lys Thr Glu Val Leu Ser Ile Ser
        305                 310                 315                 320

Asn Glu Thr Phe Pro Glu Leu Gly Val Lys Asn Asp Glu Cys Lys Glu
                            325                 330                 335

Met Thr Trp Val Glu Ser Ala Leu Phe Phe Ser Glu Leu Ala Asp Val
                        340                 345                 350

Asn Gly Asn Ser Thr Gly Asp Ile Ser Arg Leu Lys Glu Arg Tyr Met
                        355                 360                 365

Asp Gly Lys Gly Phe Phe Lys Gly Lys Thr Asp Tyr Val Lys Lys Pro
                    370                 375                 380

Val Ser Met Asp Gly Met Leu Thr Phe Leu Val Glu Leu Glu Lys Asn
        385                 390                 395                 400

Pro Lys Gly Tyr Leu Val Phe Asp Pro Tyr Gly Gly Ala Met Asp Lys
                        405                 410                 415

Ile Ser Asp Gln Ala Ile Ala Phe Pro His Arg Lys Gly Asn Leu Phe
                        420                 425                 430

Ala Ile Gln Tyr Leu Ala Gln Trp Asn Glu Glu Asp Tyr Met Ser
                    435                 440                 445

Asp Val Tyr Met Glu Trp Ile Arg Gly Phe Tyr Asn Thr Met Thr Pro
                        450                 455                 460

Phe Val Ser Ser Pro Arg Gly Ala Tyr Ile Asn Tyr Leu Asp Met
        465                 470                 475                 480

Asp Leu Gly Val Asn Met Val Asp Asp Tyr Leu Leu Arg Asn Ala Ser
                        485                 490                 495

Ser Ser Ser Pro Ser Ser Val Asp Ala Val Glu Arg Ala Arg Ala
                    500                 505                 510

Trp Gly Glu Met Tyr Phe Leu His Asn Tyr Asp Arg Leu Val Lys Ala
                    515                 520                 525

Lys Thr Gln Ile Asp Pro Leu Asn Val Phe Arg His Glu Gln Ser Ile
        530                 535                 540

Pro Pro Met Leu Gly Ser Thr Gln Glu His Lys Tyr Ser Ser Glu
        545                 550                 555

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
tcgaacggga tcccgccgct cgagcgg                                          27

<210> SEQ ID NO 6
<211> LENGTH: 24
<212> TYPE: DNA
```

<213> ORGANISM: Artificial Sequence
<220> FEATURE:
<223> OTHER INFORMATION: Description of Artificial Sequence: Synthetic
      Oligonucleotide

<400> SEQUENCE: 6
gatcagctct agagccgagc tcgc                                          24

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
ccgctcgagc ggtcagagga agatattctc ca                                 32

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
ggggtacccc tggaataaga cgaaaaatag                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
gctctagagc tcagaggaag atattctcca                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
ccatcgatgg tggaataaga cgaaaaatag                                    30

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
atggttgtat cagagaaaag                                               20

<210> SEQ ID NO 12
<211> LENGTH: 24
<212> TYPE: DNA
<213> ORGANISM: Artificial Sequence

```
<220> FEATURE:
<223> OTHER INFORMATION: Description of Artificial Sequence: Synthetic
      Oligonucleotide

<400> SEQUENCE: 12
ccttctgcct ctatcatcct cctg                                          24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
atgtttccgc tcataattct g                                             21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
tcttcgccca tggcttttcg gtct                                          24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
caaaaccaga tcgcttggtc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 16
cacagcactt acaccacctt                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
cggtggagca aaagtaagtg                                               20

<210> SEQ ID NO 18
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      Oligonucleotide

<400> SEQUENCE: 18
gaaacggaac aatcaaagca                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
tcactgctac agtgcatcct                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
ttagagcttt gccgacacct                                                    20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
cgtctcattc cacatcggta gc                                                 22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
ggtgagtaac aatggcggaa gt                                                 22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
gccatgataa tggcaacgag                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
```

Oligonucleotide

<400> SEQUENCE: 24
ttagcagcga gataagggaa                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25
agttggagga ggtgatgatg                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26
tatgtgggtc gctcaatgtc                                                  20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27
ggaaaactaa caacggaatc tct                                              23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 28
gatcaagcta ttgctttccc t                                                21

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 29
ccggaattcg cacagtggaa tgaagaggac g                                     31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

```
<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 30
ccgctcgagg cgttgaacca agcataggag g                              31

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
ccatcgatgc acagtggaat gaagaggacg                                30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32
gctctagagc gttgaaccaa gcataggagg                                30

<210> SEQ ID NO 33
<211> LENGTH: 58
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33
aaaaagcagg cttcgaagga gatagaacca tggttccgct cataattctg atcagctt   58

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 34
agaaagctgg gtcttcactg ctatacttgt gctcttga                       38

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 35
ggggacaagt ttgtacaaaa aagcaggct                                 29

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide
```

<400> SEQUENCE: 36 gggaccact ttgtacaaga aagctgggt                                    29

<210> SEQ ID NO 37
<211> LENGTH: 538
<212> TYPE: PRT
<213> ORGANISM: Eschscholzia californica

<400> SEQUENCE: 37

```
Met Glu Asn Lys Thr Pro Ile Phe Phe Ser Leu Ser Ile Phe Leu Ser
  1               5                  10                  15

Leu Leu Asn Cys Ala Leu Gly Gly Asn Asp Leu Leu Ser Cys Leu Thr
             20                  25                  30

Phe Asn Gly Val Arg Asn His Thr Val Phe Ser Ala Asp Ser Asp Ser
         35                  40                  45

Asp Phe Asn Arg Phe Leu His Leu Ser Ile Gln Asn Pro Leu Phe Gln
     50                  55                  60

Asn Ser Leu Ile Ser Lys Pro Ser Ala Ile Ile Leu Pro Gly Ser Lys
 65                  70                  75                  80

Glu Glu Leu Ser Asn Thr Ile Arg Cys Ile Arg Lys Gly Ser Trp Thr
                 85                  90                  95

Ile Arg Leu Arg Ser Gly Gly His Ser Tyr Glu Gly Leu Ser Tyr Thr
            100                 105                 110

Ser Asp Thr Pro Phe Ile Leu Ile Asp Leu Met Asn Leu Asn Arg Val
        115                 120                 125

Ser Ile Asp Leu Glu Ser Glu Thr Ala Trp Val Glu Ser Gly Ser Thr
    130                 135                 140

Leu Gly Glu Leu Tyr Tyr Ala Ile Thr Glu Ser Ser Lys Leu Gly
145                 150                 155                 160

Phe Thr Ala Gly Trp Cys Pro Thr Val Gly Thr Gly His Ile Ser
                165                 170                 175

Gly Gly Gly Phe Gly Met Met Ser Arg Lys Tyr Gly Leu Ala Ala Asp
            180                 185                 190

Asn Val Val Asp Ala Ile Leu Ile Asp Ala Asn Gly Ala Ile Leu Asp
        195                 200                 205

Arg Gln Ala Met Gly Glu Asp Val Phe Trp Ala Ile Arg Gly Gly Gly
    210                 215                 220

Gly Gly Val Trp Gly Ala Ile Tyr Ala Trp Lys Ile Lys Leu Leu Pro
225                 230                 235                 240

Val Pro Glu Lys Val Thr Val Phe Arg Val Thr Lys Asn Val Ala Ile
                245                 250                 255

Asp Glu Ala Thr Ser Leu Leu His Lys Trp Gln Phe Val Ala Glu Glu
            260                 265                 270

Leu Glu Glu Asp Phe Thr Leu Ser Val Leu Gly Gly Ala Asp Glu Lys
        275                 280                 285

Gln Val Trp Leu Thr Met Leu Gly Pro His Phe Gly Leu Lys Thr Val
    290                 295                 300

Ala Lys Ser Thr Phe Asp Leu Leu Phe Pro Glu Leu Gly Leu Val Glu
305                 310                 315                 320

Glu Asp Tyr Leu Glu Met Ser Trp Gly Glu Ser Phe Ala Tyr Leu Ala
                325                 330                 335

Gly Leu Glu Thr Val Ser Gln Leu Asn Asn Arg Phe Leu Lys Phe Asp
            340                 345                 350

Glu Arg Ala Phe Lys Thr Lys Val Asp Leu Thr Lys Glu Pro Leu Pro
```

-continued

```
            355                 360                 365
Ser Lys Ala Phe Tyr Gly Leu Leu Glu Arg Leu Ser Lys Glu Pro Asn
    370                 375                 380

Gly Phe Ile Ala Leu Asn Gly Phe Gly Gly Gln Met Ser Lys Ile Ser
385                 390                 395                 400

Ser Asp Phe Thr Pro Phe Pro His Arg Ser Gly Thr Arg Leu Met Val
                405                 410                 415

Glu Tyr Ile Val Ala Trp Asn Gln Ser Glu Gln Lys Lys Lys Thr Glu
                420                 425                 430

Phe Leu Asp Trp Leu Glu Lys Val Tyr Glu Phe Met Lys Pro Phe Val
            435                 440                 445

Ser Lys Asn Pro Arg Leu Gly Tyr Val Asn His Ile Asp Leu Asp Leu
        450                 455                 460

Gly Gly Ile Asp Trp Gly Asn Lys Thr Val Val Asn Asn Ala Ile Glu
465                 470                 475                 480

Ile Ser Arg Ser Trp Gly Glu Ser Tyr Phe Leu Ser Asn Tyr Glu Arg
                485                 490                 495

Leu Ile Arg Ala Lys Thr Leu Ile Asp Pro Asn Asn Val Phe Asn His
                500                 505                 510

Pro Gln Ser Ile Pro Pro Met Ala Asn Phe Asp Tyr Leu Glu Lys Thr
            515                 520                 525

Leu Gly Ser Asp Gly Gly Glu Val Val Ile
530                 535
```

METHODS AND COMPOSITIONS FOR IDENTIFYING NBB1 MUTATIONS

CROSS-REFERENCE TO RELATED APPLICATIONS

This application is a divisional of U.S. patent application Ser. No. 14/685,361, filed Apr. 13, 2015, which is a divisional of U.S. patent application Ser. No. 13/082,953, filed Apr. 8, 2011, now U.S. Pat. No. 9,029,656, which is a continuation of U.S. patent application Ser. No. 11/579,661, filed Nov. 6, 2006, now U.S. Pat. No. 8,791,329, which is the National Phase of International Patent Application No. PCT/IB2006/001741, filed Feb. 28, 2006, which claims priority from U.S. Provisional Patent Application No. 60/656,536, filed Feb. 28, 2005. The contents of these applications are incorporated herein by reference in their entirety.

FIELD OF THE INVENTION

The present invention relates to the field of molecular biology and the down-regulation of alkaloid synthesis. More specifically, the invention relates to methodology and constructs for reducing nicotinic alkaloids in a plant, particularly but not exclusively in a tobacco plant.

BACKGROUND OF THE INVENTION

Presently, several methods exist for reducing nicotinic alkaloids, such as nicotine, in plants. A low-nicotine strain of tobacco has been employed, for instance, as breeding stock for low-nicotine cultivars. Legg et al., *Crop Sci* 10:212 (1970). Genetic engineering methods also can be used to reduce nicotine levels. For example, U.S. Pat. No. 5,369,023, and No. 5,260,205 discuss decreasing nicotine levels via antisense targeting of an endogenous putrescine methyl transferase (PMT) sequence. Voelckel et al., *Chemoecology* 11:121-126 (2001). The tobacco quinolate phosphoribosyl transferase (QPT) gene has been cloned, Sinclair et al., *Plant Mol. Biol.* 44: 603-617 (2000), and its antisense suppression provided significant nicotine reductions in transgenic tobacco plants. Xie et al., *Recent Advances in Tobacco Science* 30: 17-37 (2004). See also U.S. Pat. Nos. 6,586,661 and 6,423,520.

Several nicotine biosynthesis enzymes are known. For instance, see Hashimoto et al., *Plant Mol. Biol.* 37:25-37 (1998); Reichers & Timko, *Plant Mol. Biol.* 41:387-401 (1999); Imanishi et al., *Plant Mol. Biol.* 38:1101-1111 (1998). Still, there is a continuing need for additional genetic engineering methods for further reducing nicotinic alkaloids. When only PMT is down-regulated in tobacco, for example, nicotine is reduced but anatabine increases by about 2-to-6-fold. Chintapakorn & Hamill, *Plant Mol. Biol.* 53: 87-105 (2003); Steppuhn, et al., *PLoS Biol* 2(8): e217: 1074-1080 (2004). When only QPT is down-regulated, a fair amount of alkaloids remain. See U.S. Plant Variety Certificate No. 200100039.

Reducing total alkaloid content in tobacco would increase the value of tobacco as a biomass resource. When grown under conditions that maximize biomass, such as high density and multiple cuttings, tobacco can yield more than 8 tons dry weight per acre, which is comparable with other crops used for biomass. Large-scale growing and processing of conventional tobacco biomass has several drawbacks, however. For example, significant time and energy is spent extracting, isolating, and disposing tobacco alkaloids because conventional tobacco biomass, depending on the variety, contains about 1 to about 5 percent alkaloids. On a per acre basis, conventional tobacco biomass contains approximately as much as 800 pounds of alkaloids. Also, people handling tobacco may suffer from overexposure to nicotine, commonly referred to as "green tobacco disease."

Reduced-alkaloid tobacco is more amenable for non-traditional purposes, such as biomass and derived products. For example, it is advantageous to use reduced-alkaloid tobacco for producing ethanol and protein co-products. U.S. published application No. 2002/0197688. Additionally, alkaloid-free tobacco or fractions thereof may be used as a forage crop, animal feed, or a human nutritive source. Id.

Beyond these benefits associated with reducing nicotine, more successful methods are needed to assist smokers in quitting smoking. Nicotine replacement therapy (NRT) is not very effective as a smoking cessation treatment because its success rate is less than 20 percent after 6 to 12-months from the end of the nicotine replacement period. Bohadana et al., *Arch Intern. Med.* 160:3128-3134 (2000); Croghan et al., *Nicotine Tobacco Res.* 5:181-187 (2003); Stapleton et al., *Addiction* 90:31-42 (1995). Nicotine-reduced or nicotine-free tobacco cigarettes have assisted smokers in quitting smoking successfully, by weaning the smoker from nicotine yet allowing the smoker to perform the smoking ritual. Additionally, denicotinized cigarettes relieve craving and other smoking withdrawal symptoms. See Rose, *Psychopharmacology* 184: 274-285 (2006) and Rose et al., *Nicotine Tobacco Res.* 8:89-101 (2006).

Accordingly, there is a continuing need to identify additional genes whose expression can be affected to decrease nicotinic alkaloid content.

SUMMARY OF THE INVENTION

Two genes, A622 and NBB1, can be influenced to achieve a decrease of nicotinic alkaloid levels in plants. In particular, suppression of one or both of A622 and NBB1 may be used to decrease nicotine in tobacco plants.

Accordingly, in one aspect, the invention provides an isolated nucleic acid molecule comprising a nucleotide sequence selected from (a) a nucleotide sequence set forth in SEQ ID NO: 3; (b) a nucleotide sequence that encodes a polypeptide having the amino acid sequence set forth in SEQ ID NO: 4; and (c) a nucleotide sequence that differs from the nucleotide sequences of (a) or (b) due to degeneracy of the genetic code and encodes a polypeptide with NBB1 expression.

In another aspect, the invention provides an isolated nucleic acid molecule comprising a nucleotide sequence selected from (a) a nucleotide sequence set forth in SEQ ID NO: 1; (b) a nucleotide sequence that encodes a polypeptide having the amino acid sequence set forth in SEQ ID NO: 2; and (c) a nucleotide sequence that differs from the nucleotide sequences of (a) or (b) due to degeneracy of the genetic code and encodes a polypeptide with A622 expression, wherein said nucleotide sequence is operatively linked to a heterologous promoter.

In another aspect, the invention provides a method for reducing an alkaloid in a plant, comprising decreasing NBB1 and A622 expression.

In another aspect, the invention provides a transgenic plant having reduced A622 expression and alkaloid content, as well as a tobacco plant having reduced NBB1 expression and alkaloid content. The invention provides also a genetically engineered plant having reduced nicotine and anatabine content.

In another aspect, the invention provides a reduced-nicotine tobacco product made from a tobacco plant having reduced A622 or NBB1 expression.

BRIEF DESCRIPTION OF THE DRAWINGS

FIG. 10 depicts an alignment of NBB1 (SEQ ID NO: 4) with *Eschscholzia californica* berberine bridge enzyme (EcBBE) (SEQ ID NO: 37).

DETAILED DESCRIPTION OF THE INVENTION

Figure 1:
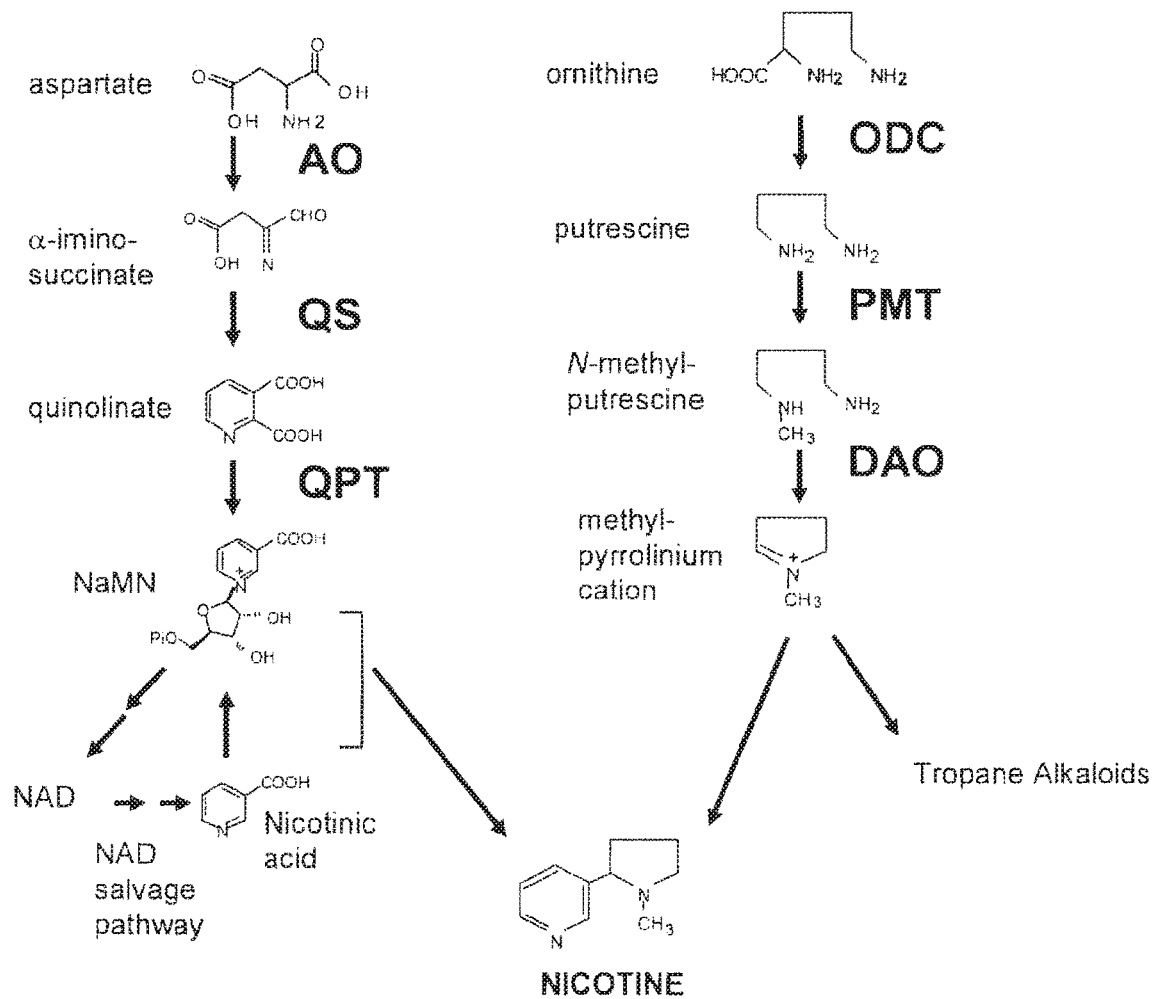
FIG. 1 depicts the nicotine biosynthesis pathway. The abbreviations are: AO=aspartate oxidase, QS=quinolinate synthase, QPT=quinolinate phosphoribosyl transferase, ODC=ornithine decarboxylase, PMT=putrescine N-methyltransferase, and DAO=diamine oxidase.

The present inventors identified two genes, A622 and NBB1, that can be influenced to achieve a decrease of nicotinic alkaloid levels in plants, including but not limited to tobacco. While A622 was identified previously by Hibi et al. *Plant Cell* 6: 723-735 (1994), the present inventors discovered a role for A622, heretofore unknown, in the context of decreasing nicotine biosynthesis. The field was wholly unaware of NBB1, before the inventor's discovery, and they also elucidated a role for NBB1 in an approach, according to the present invention, for reducing nicotinic alkaloid content in plants.

Accordingly, the present invention encompasses both methodology and constructs for reducing nicotinic alkaloid content in a plant, by suppressing A622 or NBB1 expression. That is, nicotinic alkaloid levels can be reduced by suppressing one or both of A622 and NBB1. Pursuant to this aspect of the invention, a plant or any part thereof is transformed with a nucleotide sequence, expression of which suppresses at least one of A622 and NBB1 and reduces nicotinic alkaloid content.

In another aspect of the invention, nicotine can be further suppressed in a plant by concurrently suppressing expression of any known enzyme in the nicotine biosynthesis pathway, such as QPT or PMT, and at least one of A622 and NBB1. In addition to decreasing nicotine, for example, the present invention provides a means for concurrently reducing anatabine. Thus, anatabine levels can be lowered by suppressing a nicotine biosynthesis gene, such as QPT, and at least one of A622 and NBB1.

By means of affecting A622 and/or NBB1 expression, to the ends of reducing nicotinic alkaloid content in a plant, numerous reduced-alkaloid plants and by-products may be obtained, in keeping with the present invention. For example, a tobacco plant having suppressed A622 or NBB1 expression may be used for producing reduced-nicotine cigarettes, which may find use as a smoking cessation product. Likewise, reduced-nicotine tobacco may be used as a forage crop, animal feed, or a source for human nutrition.

Other objects, features and advantages of the present invention will become apparent from the following detailed description. It should be understood, however, that the detailed description and the specific examples, while indicating preferred embodiments of the invention, are given by way of illustration only, since changes and modifications within the spirit and scope of the invention may become apparent to those of skill in the art from this detailed description.

Definitions

The technical terms employed in this specification are commonly used in biochemistry, molecular biology and agriculture; hence, they are understood by those skilled in the field to which this invention belongs. Those technical terms can be found, for example in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997.

Methodology involving plant biology techniques are described herein and are described in detail in methodology treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, for example, in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage & Caruthers, *Tetra. Letts.* 22:1859-1862 (1981), and Matteucci & Caruthers, *J. Am. Chem. Soc.* 103:3185 (1981).

Restriction enzyme digestions, phosphorylations, ligations and transformations were done as described in Sambrook et al., MOLECULAR CLONING: A LABORATORY MANUAL, $2^{nd}$ ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

A622 expression is controlled by the NIC1 and NIC2 gene loci in tobacco plants. Hibi et al., *The Plant Cell,* 6: 723-735 (1994). It has been reported that A622 exhibits the same expression pattern as PMT. Shoji, T. et al., *Plant Cell Physiol.*, 41:9:1072-1076 (2000a); Shoji, T., et al., *Plant Mol Biol,* 50:427-440 (2002). Both A622 and PMT are expressed specifically in roots, particularly in the cortex and endodermis of the apical parts of the roots and root hairs. Shoji et al. (2002). Moreover, A622 and PMT have a common pattern of expression in response to NIC regulation and methyl-jasmonate stimulus. A622 is induced in the roots of *Nicotiana tabacum* in response to wounding of aerial tissues. Cane et al., *Functional Plant Biology,* 32, 305-320 (2005). In *N. glauca,* A622 is induced in wounded leaves under conditions that result in QPT induction. Sinclair et al., *Func. Plant Biol.,* 31:721-9 (2004).

The nucleic acid sequence of A662 (SEQ ID NO: 1) has been determined. Hibi et al. (1994), supra. The protein encoded by this nucleic acid sequence (SEQ ID NO: 2) resembles isoflavone reductases (IFR) and contains an NADPH-binding motif. A622 shows homology to TP7, a tobacco phenylcoumaran benzylic ether reductase (PCBER) involved in lignin biosynthesis. Shoji et al. (2002), supra. No PCBER activity was observed, however, when A622 expressed in *E. coli* was assayed with two different substrates.

Based on co-regulation of A622 and PMT and the similarity of A622 to IFR, A622 was proposed to function as a reductase in the final steps of nicotinic alkaloid synthesis. Hibi et al. (1994); Shoji, et al. (2000a). No IFR activity was observed, however, when the protein was expressed in bacteria (id.). The function of A622 was unknown previously, and there was no understanding heretofore that A622 plays a role in nicotine synthesis.

A622 expression refers to biosynthesis of a gene product encoded by SEQ ID NO: 1. A622 suppression refers to the reduction of A622 expression. A622 suppression has an ability to down-regulate nicotinic alkaloid content in a plant or a plant cell.

An alkaloid is a nitrogen-containing basic compound found in plants and produced by secondary metabolism. A nicotinic alkaloid is nicotine or an alkaloid that is structurally related to nicotine and that is synthesized from a compound produced in the nicotine biosynthesis pathway. In the case of tobacco, nicotinic alkaloid content and total alkaloid content are used synonymously.

Illustrative *Nicotiana* alkaloids include but are not limited to nicotine, nornicotine, anatabine, anabasine, anatalline, N-methylanatabine, N-methylanabasine, myosmine, anabaseine, N'-formylnornicotine, nicotyrine, and cotinine. Other very minor alkaloids in tobacco leaf are reported, for example, in Hecht, S. S. et al., *Accounts of Chemical Research* 12: 92-98 (1979); Tso, T. C., Production, *Physiology and Biochemistry of Tobacco Plant.* Ideals Inc., Beltsville, Md. (1990). The chemical structures of several alkaloids are presented, for example, in Felpin et al., *J. Org. Chem.* 66: 6305-6312 (2001).

Nicotine is the primary alkaloid in *N. tabacum* along with 50-60 percent of other species of *Nicotiana*. Based on alkaloid accumulation in the leaves, nornicotine, anatabine, and anabasine are the other foremost alkaloids in *N. tabacum. Anatabine is usually not the primary alkaloid in any species but does accumulate to relatively higher amounts in 3 species; anabasine is the primary alkaloid in four species.* Nomicotine is the primary alkaloid in 30 to 40 percent of *Nicotiana* species. Depending on the variety, about 85 to about 95 percent of total alkaloids in *N. tabacum* is nicotine. Bush, L. P., *Tobacco Production, Chemistry and Technology,* Coresta 285-291 (1999); Hoffmann, et al., *Journal of Toxicology and Environmental Health,* 41:1-52, (1994).

In the present invention, nicotinic alkaloid content can be reduced in a genetically engineered plant by down-regulating at least one of A622 and NBB1. Additionally, a nicotinic alkaloid content can be lowered by down-regulating a nicotine biosynthesis enzyme, such as QPT or PMT, and at least one of A622 and NBB1.

Anatabine is a nicotinic alkaloid. Previous studies have demonstrated that PMT suppression reduces nicotine content but increases putrescine and anatabine levels. Chintapakorn & Hamill, *Plant Mol. Biol.* 53: 87-105 (2003); Sato et al., *Proc. Natl. Acad Sci. USA* 98, 367-372. (2001); Steppuhn, A., et al., *PLoS Biol* 2(8): e217: 1074-1080 (2004). For the purposes of the present invention, anatabine content can be lowered in a genetically engineered plant by down-regulating at least one of A622 and NBB1. Anatabine levels can be lowered further by down-regulating a nicotine biosynthesis enzyme, such as QPT, and at least one of A622 and NBB1.

A BY-2 Tobacco Cell is a cell line established in 1960s by Japan Tobacco Co., Ltd. from a tobacco variety Bright Yellow-2. Since this cell line grows very fast in tissue culture, it is easy to grow on a large scale and is amenable for genetic manipulation. A BY-2 tobacco cell is widely used as a model plant cell line in basic research. When cultured in a standard medium, a BY-2 tobacco cell does not produce nicotinic alkaloids. Addition of jasmonate into the culture medium induces formation of nicotinic alkaloids.

Complementary DNA (cDNA) is a single-stranded DNA molecule that is formed from an mRNA template by the enzyme reverse transcriptase. Those skilled in the art also use "cDNA" to denote to a double stranded DNA molecule that includes such a single-stranded DNA molecule and its complementary DNA strand. Typically, a primer complementary to portions of mRNA is employed for the initiation of a reverse transcription process that yields a cDNA.

Expression refers to the biosynthesis of a gene product. In the case of a structural gene, for example, expression involves transcription of the structural gene into mRNA and the translation of the mRNA into one or more polypeptides.

Gene refers to a polynucleotide sequence that comprises control and coding sequences necessary for the production of a polypeptide or precursor. The polypeptide can be encoded by a full-length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

Genetically engineered (GE) encompasses any methodology for introducing a nucleic acid or specific mutation into a host organism. For example, a tobacco plant is genetically engineered when it is transformed with a polynucleotide sequence that suppresses expression of a gene, such as A622 or NBB1, and thereby reduces nicotine levels. In contrast, a tobacco plant that is not transformed with a polynucleotide sequence that suppresses expression of a target gene is a control plant and is referred to as a "non-transformed" plant.

In the present context, the "genetically engineered" category includes "transgenic" plants and plant cells (see definition, infra), as well as plants and plant cells produced by means of targeted mutagenesis effected, for example, through the use of chimeric RNA/DNA oligonucleotides, as described by Beetham et al., *Proc. Nat'l. Acad. Sci. USA* 96: 8774-8778 (1999) and Zhu et al., loc. cit. at 8768-8773, or so-called "recombinagenic olionucleobases," as described in PCT application WO 03/013226. Likewise, a genetically engineered plant or plant cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or plant cell may be the product of any native approach (i.e., involving no foreign nucleotide sequences), implemented by introducing only nucleic acid sequences derived from the host plant species or from a sexually compatible plant species. See, e.g., U.S. published application No. 2004/0107455.

A genomic library is a collection of clones that contains at least one copy of essentially every DNA sequence in the genome.

The NBB1 sequence was identified by cDNA microarray prepared from a *Nicotiana sylvestris*-derived cDNA library, pursuant to the protocol of Katoh et al., *Proc. Japan Acad.*, 79 (Ser. B): 151-154 (2003). NBB1 also is controlled by the nicotine biosynthesis regulatory loci, NIC1 and NIC2. NBB1 and PMT have the same pattern of expression in tobacco plants. That NBB1 is involved in nicotine biosynthesis is indicated by the fact that NBB1, like PMT and A622, is under the control of the NIC genes and exhibits a similar pattern of expression.

NBB1 expression refers to biosynthesis of a gene product encoded by SEQ ID NO: 3. NBB1 suppression refers to the reduction of NBB1 expression.

NBB1 suppression has an ability to down-regulate nicotinic alkaloid content.

NIC1 and NIC2 loci are two independent genetic loci in *N. tabacum*, formerly designated as A and B. Mutations nic1 and nic2 reduce expression levels of nicotine biosynthesis enzymes and nicotine content, generally the nicotine content of wild type>homozygous nic2>homozygous nic1>homoyzgous nic1 and homozygous nic2 plants. Legg & Collins, *Can. J. Cyto.* 13:287 (1971); Hibi et al., *Plant Cell* 6: 723-735 (1994); Reed & Jelesko, *Plant Science* 167:1123 (2004).

Nicotine is the major alkaloid in *N. tabacum* and some other species in the *Nicotiana* genus. Other plants have nicotine-producing ability, including, for example, *Duboisia, Anthocericis* and *Salpiglessis* genera in the Solanaceae, and Eclipta and *Zinnia* genera in the Compositae.

Plant is a term that encompasses whole plants, plant organs (e. g. leaves, stems, roots, etc.), seeds, and plant cells and progeny of the same. Plant material includes, without limitation, seeds suspension cultures, embryos, meristematic regions, callus tissues, leaves, roots and shoots, gametophytes, sporophytes, pollen, and microspores. The class of plants which can be used in the present invention is generally as broad as the class of higher plants amenable to transformation techniques, including both monocotyledonous and dicotyledonous plants. A preferred plant is a plant having nicotine-producing ability of the *Nicotiana, Duboisia, Anthocericis* and *Salpiglessis* genera in the Solanaceae or the Eclipta and *Zinnia* genera in the Compositae. A particularly preferred plant is *Nicotiana tabacum*.

Protein refers to a polymer of amino acid residues.

Reduced-nicotine plant encompasses a genetically engineered plant that contains less than half, preferably less than 25%, and more preferably less than 20% or less than 10% of the nicotine content of a non-transgenic control plant of the same type. A reduced-nicotine plant also includes a genetically engineered plant that contains less total alkaloids compared with a control plant.

A structural gene refers to a DNA sequence that is transcribed into messenger RNA (mRNA) which is then translated into a sequence of amino acids characteristic of a specific polypeptide. "Messenger RNA (mRNA)" denotes an RNA molecule that contains the coded information for the amino acid sequence of a protein.

Sequence identity or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties, such as charge and hydrophobicity, and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4: 11-17 (1988), as implemented in the program PC/GENE (Intelligenetics, Mountain View, Calif., USA).

Use in this description of a percentage of sequence identity denotes a value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Sequence identity has an art-recognized meaning and can be calculated using published techniques. See COMPUTATIONAL MOLECULAR BIOLOGY, Lesk, ed. (Oxford University Press, 1988), BIOCOMPUTING: INFORMATICS AND GENOME PROJECTS, Smith, ed. (Academic Press, 1993), COMPUTER ANALYSIS OF SEQUENCE DATA, PART I, Griffin & Griffin, eds., (Humana Press, 1994), SEQUENCE ANALYSIS IN MOLECULAR BIOLOGY, Von Heinje ed., Academic Press (1987), SEQUENCE ANALYSIS PRIMER, Gribskov & Devereux, eds. (Macmillan Stockton Press, 1991), and Carillo & Lipton, *SIAM J. Applied Math.* 48: 1073 (1988). Methods commonly employed to determine identity or similarity between two sequences include but are not limited to those disclosed in GUIDE TO HUGE COMPUTERS, Bishop, ed., (Academic Press, 1994) and Carillo & Lipton, supra. Methods to determine identity and similarity are codified in computer programs. Preferred computer program methods to determine identity and similarity between two sequences include but are not limited to the GCG program package (Devereux et al., *Nucleic Acids Research* 12: 387 (1984)), BLASTP, BLASTN, FASTA (Atschul et al., *J. Mol. Biol.* 215: 403 (1990)), and FASTDB (Brutlag et al., *Comp. App. Biosci.* 6: 237 (1990)).

Tobacco refers to any plant in the *Nicotiana* genus that produces nicotinic alkaloids. Tobacco also refers to products comprising material produced by a *Nicotiana* plant, and therefore includes, for example, cigarettes, cigars, chewing tobacco, snuff and cigarettes made from GE reduced-nicotine tobacco for use in smoking cessation. Examples of *Nicotiana* species include but are not limited to *N. alata, N. glauca, N. longiflora, N. persica, N. rustica, N. sylvestris,* and *N. tabacum.*

Tobacco-specific nitrosamines (TSNAs) are a class of carcinogens that are predominantly formed in tobacco during curing, processing, and smoking. Hoffman, D., et al., *J. Natl. Cancer Inst.* 58, 1841-4 (1977); Wiernik A et al., Recent Adv. Tob. Sci, (1995), 21: 39-80. TSNAs, such as 4-(N-nitrosomethylamino)-1-(3-pyridyl)-1-butanone (NNK), N'-nitrosonornicotine (NNN), N'-nitrosoanatabine (NAT), and N'-nitrosoanabasine (NAB), are formed by N-nitrosation of nicotine and other minor *Nicotiana* alkaloids, such as nornicotine, anatabine, and anabasine. Reducing nicotinic alkaloids reduces the level of TSNAs in tobacco and tobacco products.

Tobacco hairy roots refers to tobacco roots that have T-DNA from an Ri plasmid of *Agrobacterium rhizogenes* integrated in the genome and grow in culture without supplementation of auxin and other pytohormones. Tobacco hairy roots produce nicotinic alkaloids as roots of a tobacco plant do.

Transgenic plant refers to a plant that comprises a nucleic acid sequence that also is present per se in another organism or species or that is optimized, relative to host codon usage, from another organism or species.

A transgenic plant may be produced by any genetic transformation methodology. Suitable transformation methods include, for example, *Agrobacterium*-mediated transformation, particle bombardment, electroporation, polyethylene glycol fusion, transposon tagging, and site-directed mutagenesis. Identification and selection of a transgenic plant are well-known techniques, the details of which need not be repeated here.

A variant is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents.

The present invention is not limited to the particular methodology, protocols, vectors, and reagents, etc., described here, as these may vary. Furthermore, this specification employs the above-discussed terminology for the purpose of describing particular embodiments only and not to limit the scope of the invention.

The singular forms "a," "an," and "the" include plural reference unless the context clearly dictates otherwise. Thus, a reference to "a gene" is a reference to one or more genes and encompasses equivalents thereof that are known to the skilled person, and so forth.

Polynucleotide Sequences

Nicotinic alkaloid biosynthesis genes have been identified in several plant species, exemplified by *Nicotiana* plants. Accordingly, the present invention embraces any nucleic acid, gene, polynucleotide, DNA, RNA, mRNA, or cDNA molecule that is isolated from the genome of a plant species that down-regulates nicotinic alkaloid biosynthesis.

For example, suppression of at least one of A622 and NBB1, may be used to down-regulate nicotine content in a plant. Additionally, nicotinic alkaloid levels can be reduced further by suppressing expression of a nicotine biosynthesis gene, such as at least one of QPT and PMT, and at least one of A622 and NBB1. Plants with suppression of multiple genes may be obtained by regeneration of plants from plant cells genetically engineered for suppression of multiple genes or by crossing a first plant genetically engineered for suppression of a nicotine biosynthesis gene with a second plant genetically engineered for suppression of at least one of A622 and NBB1.

In one aspect, the invention provides an isolated nucleic acid molecule comprising SEQ ID NO: 1; polynucleotide sequences encoding a polypeptide set forth in SEQ ID NO: 2; polynucleotide sequences which hybridize to SEQ ID NO: 1 and encode an A622 polypeptide; and polynucleotide sequences which differ from SEQ ID NO: 1 due to the degeneracy of the genetic code. A peptide encoded by SEQ ID NO: 1 is a further aspect of the invention and is set forth in SEQ ID NO: 2.

In another aspect, the invention provides an isolate nucleic acid molecule comprising SEQ ID NO: 3; polynucleotide sequences encoding a polypeptide set forth in SEQ ID NO: 4; polynucleotide sequences which hybridize to SEQ ID NO: 3 and encode an NBB1 polypeptide; and polynucleotide sequences which differ from SEQ ID NO: 3 due to the degeneracy of the genetic code. A peptide encoded by SEQ ID NO: 3 is a further aspect of the invention and is set forth in SEQ ID NO: 4

The invention further provides nucleic acids that are complementary to SEQ ID NO: 1 or 3, as well as a nucleic acid, comprising at least 15 contiguous bases, that hybridizes to SEQ ID NO: 1 or 3 under moderate or high stringency conditions, as described below. For the purposes of this description, the category of nucleic acids that hybridize to SEQ ID NO: 3 is exclusive of a nucleic acid having the sequence of SEQ ID NO: 559, disclosed in published international application WO 03/097790, and of any fragment thereof.

In a further embodiment, a siRNA molecule of the invention comprises a polynucleotide sequence that suppresses expression of either of SEQ ID NO. 1 or 3, although the sequences set forth in SEQ ID NO: 1 or 3 are not limiting. A siRNA molecule of the invention can comprise any contiguous A622 or NBB1 sequence, e.g., about 15 to about 25 or more, or about 15, 16, 17, 18, 19, 20, 21, 22, 23, 24, or 25 or more contiguous nucleotides. In this context, too, the category of siRNA molecules is exclusive of a molecule having the nucleotide sequence of the aforementioned SEQ ID NO: 559 in WO 03/097790, as well as any fragment thereof.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also called the anti-sense strand.

Unless otherwise indicated, all nucleotide sequences determined by sequencing a DNA molecule herein were determined using an automated DNA sequencer (such as the Model 373 from Applied Biosystems, Inc.). Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

In another aspect, the invention provides an isolated nucleic acid molecule comprising a polynucleotide that hybridizes, under stringent hybridization conditions, to a portion of the polynucleotide in a nucleic acid molecule of the invention, as described above. By a polynucleotide that hybridizes to a "portion" of a polynucleotide is intended a polynucleotide, either DNA or RNA, hybridizing to at least about 15 nucleotides, and more preferably at least about 20 nucleotides, and still more preferably at least about 30 nucleotides, and even more preferably more than 30 nucleotides of the reference polynucleotide.

For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

The present application is directed to such nucleic acid molecules which are at least 60%, 65%, 70%, 75%, 80%, 85%, 90%, 95%, 96%, 97%, 98%, 99% or 100% identical to a nucleic acid sequence described in of SEQ ID NO: 1 or 3. Preferred are nucleic acid molecules which are at least 95%, 96%, 97%, 98%, 99% or 100% identical to the nucleic acid sequence shown in of SEQ ID NO: 1 or 3. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25: 3389-3402 (1997).

The heterologous sequence utilized in the antisense methods of the present invention may be selected so as to produce an RNA product complementary to an entire A622 or NBB1 mRNA sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA.

Suitable antisense sequences may be from at least about 13 to about 15 nucleotides, at least about 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof.

The particular antisense sequence and the length of the antisense sequence will vary, depending, for example, upon the degree of inhibition desired and the stability of the antisense sequence. Generally available techniques and the information provided in this specification can guide the selection of appropriate A622 or NBB1 antisense sequences. With reference to SEQ ID NO: 1 or 3 herein, an oligonucleotide of the invention may be a continuous fragment of A622 or NBB1 cDNA sequence in antisense orientation, of any length that is sufficient to achieve the desired effects when transformed into a recipient plant cell.

The present invention may contemplate sense co-suppression of one or both of A622 and NBB1. Sense polynucleotides employed in carrying out the present invention are of a length sufficient to suppress, when expressed in a plant cell, the native expression of the plant A622 or NBB1 protein in that plant cell. Such sense polynucleotides may be essentially an entire genomic or complementary nucleic acid encoding the A622 or NBB1 enzyme, or a fragment thereof, with such fragments typically being at least 15 nucleotides in length. Techniques are generally available for ascertaining the length of sense DNA that results in suppression of the expression of a native gene in a cell.

In an alternate embodiment of the present invention, plant cells are transformed with a nucleic acid construct containing a polynucleotide segment encoding an enzymatic RNA molecule (a "ribozyme"), which enzymatic RNA molecule is directed against (i.e., cleaves) the mRNA transcript of DNA encoding A622 or NBB1, as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif.

Ribozyme cleavage sites within an RNA target may initially be identified by scanning the target molecule for ribozyme cleavage sites (e.g., GUA, GUU or GUC sequences). Once identified, short RNA sequences of 15, 20, 30, or more ribonucleotides corresponding to the region of the target gene containing the cleavage site may be evaluated for predicted structural features.

The suitability of candidate targets also may be evaluated by testing their accessibility to hybridization with complimentary oligonucleotides, using ribonuclease protection assays as are known in the art. DNA encoding enzymatic RNA molecules may be produced in accordance with known techniques. For example, see Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al., U.S. Pat. No. 5,595,877; Wagner et al., U.S. Pat. No. 5,591,601; and U.S. Pat. No. 5,622,854.

Production of such an enzymatic RNA molecule in a plant cell and disruption of A622 or NBB1 protein production reduces protein activity in plant cells, in essentially the same manner as production of an antisense RNA molecule; that is, by disrupting translation of mRNA in the cell which produces the enzyme. The term "ribozyme" describes an RNA-containing nucleic acid that functions as an enzyme, such as an endoribonuclease, and may be used interchangeably with "enzymatic RNA molecule."

The present invention further includes nucleic acids encoding ribozymes, nucleic acids that encode ribozymes and that have been inserted into an expression vector, host cells containing such vectors, and methodology employing ribozymes to decrease A622 and NBB1 expression in plants.

In one embodiment, the present invention provides double-stranded nucleic acid molecules of that mediate RNA interference gene silencing. In another embodiment, the siNA molecules of the invention consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In yet another embodiment, siNA molecules of the invention comprise duplex nucleic acid molecules with overhanging ends of about 1 to about 32 (e.g., about 1, 2, or 3) nucleotides, for example, about 21-nucleotide duplexes with about 19 base pairs and 3'-terminal mononucleotide, dinucleotide, or trinucleotide overhangs. In yet another embodiment, siNA molecules of the invention comprise duplex nucleic acid molecules with blunt ends, where both ends are blunt, or alternatively, where one of the ends is blunt.

An siNA molecule of the present invention may comprise modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

For example, A622 and NBB1 expression may be decreased through genetic engineering methods that are well known in the art. Expression can be reduced by introducing a nucleic acid construct that results in expression of an RNA comprising a portion of a sequence encoding A622 or NBB1. The portion of the sequence may be in the sense or antisense orientation. The portion of the sequence may be present in inverted repeats capable of forming a double-stranded RNA region. Expression may be reduced by introducing a nucleic acid construct encoding an enzymatic RNA molecule (i.e., a "ribozyme"), which enzymatic RNA molecule is directed against (i.e., cleaves) the mRNA transcript of DNA encoding A622 or NBB1. Expression may be reduced by introducing a nucleic acid comprising a portion of an A622 or NBB1 sequence that causes targeted in situ mutagenesis of an endogenous gene, resulting in its inactivation In one embodiment of the present invention, plant cells are transformed with a nucleic acid construct containing a mutant allele of one or both of A622 and NBB1 that comprises a polynucleotide sequence that suppresses expression of one or both of A622 and NBB1. Mutant alleles according to the invention may arise from antisense sequence suppression of one or both of A622 and NBB1, or sense co-suppression of one or both of A622 and NBB1, as described herein. Thus, a mutant allele according to the invention may comprises an antisense nucleic acid sequence that expresses a short interfering RNA that suppresses expression of one or both of A622 and NBB1 or expression of a gene product encoded by SEQ ID NO: 1 or SEQ ID NO: 3. In an alternative embodiment, the mutant allele may comprise a sense nucleic acid sequence that suppresses expression of one or both of A622 and NBB1 or expression of a gene product encoded by SEQ ID NO: 1 or SEQ ID NO: 3. In yet another embodiment, the mutant allele according to the invention comprises a nucleic acid sequence that encodes a ribozyme which cleaves one or both of A622 and NBB1 transcripts. In a preferred embodiment, mutant alleles are at least 60%, 65%, 70%, 75%, 80%, 85%, 90%, 95%, 96%, 97%, 98%, or 99% identical to a nucleic acid sequence described in of SEQ ID NO: 1 or 3. Preferred are mutant alleles which are at least 95%, 96%, 97%, 98%, 99% or 100% identical to the nucleic acid sequence set forth in SEQ ID NO: 1 or 3. Differences between two mutant alleles may occur at the 5' or 3' terminal positions of the reference nucleotide sequence or anywhere between those terminal positions, interspersed either individually among nucleotides in the reference sequence or in one or more contiguous groups within the reference sequence.

Sequence Analysis

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci. USA* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, CABIOS 5: 151-153 (1989); Corpet et al., *Nucleic Acids Research*, 16: 10881-90 (1988); Huang et al., *Computer Applications in the Biosciences* 8: 155-65 (1992), and Pearson et al., *Methods in Molecular Biology* 24: 307-331 (1994).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., Eds., Greene Publishing and Wiley-Interscience, New York (1995); Altschul et al., *J. Mol. Biol.* 215:403-410 (1990); and, Altschul et al., *Nucleic Acids Res.* 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, *Proc. Natl. Acad. Sci. USA* 89:10915 (1998).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

Multiple alignment of the sequences can be performed using the CLUSTAL method of alignment (Higgins & Sharp, *CABIOS* 5:151-153 (1989)) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The following running parameters are preferred for determining alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN, FASTA, or BLASTP algorithms set at parameters described above. Alternatively, variant polynucleotides of the present invention hybridize to the polynucleotide sequence of SEQ ID NO: 1 or 3, or complements, reverse sequences, or reverse complements of those sequences, under stringent conditions.

The present invention also encompasses polynucleotides that differ from the disclosed sequences but that, as a consequence of the degeneracy of the genetic code, encode a polypeptide which is the same as that encoded by a polynucleotide of the present invention. Thus, polynucleotides comprising sequences that differ from the polynucleotide sequences recited in SEQ ID NO: 1 or 3 or complements, reverse sequences, or reverse complements thereof, as a result of conservative substitutions are contemplated by and encompassed within the present invention. Additionally, polynucleotides comprising sequences that differ from the polynucleotide sequences recited in SEQ ID NO: 1 or 3, or complements, reverse complements or reverse sequences thereof, as a result of deletions and/or insertions totaling less than 10% of the total sequence length are also contemplated by and encompassed within the present invention.

In addition to having a specified percentage identity to an inventive polynucleotide sequence, variant polynucleotides preferably have additional structure and/or functional features in common with the inventive polynucleotide. In addition to sharing a high degree of similarity in their primary structure to polynucleotides of the present invention, polynucleotides having a specified degree of identity to, or capable of hybridizing to an inventive polynucleotide preferably have at least one of the following features: (i) they contain an open reading frame or partial open reading frame encoding a polypeptide having substantially the same functional properties as the polypeptide encoded by the inventive polynucleotide; or (ii) they have domains in common. For example, a variant polynucleotide may encode a polypeptide having the ability to suppress A622 or NBB1.

Nucleic Acid Constructs

In accordance with one aspect of the invention, a sequence that reduces nicotinic alkaloid biosynthesis is incorporated into a nucleic acid construct that is suitable for plant transformation. For example, such a nucleic acid construct can be used to decrease at least one of A622 or NBB1 gene expression in plants. Additionally, an inventive nucleic acid construct may decrease one or both of A622 and NBB1 expression, as well as a polynucleotide sequence encoding a nicotine biosynthesis enzyme.

Accordingly, nucleic acid constructs are provided that comprise a sequence that down-regulates nicotinic alkaloid biosynthesis, under the control of a transcriptional initiation region operative in a plant, so that the construct can generate RNA in a host plant cell.

Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence then is cloned into a vector containing suitable regulatory elements, such as upstream promoter and downstream terminator sequences.

Suitable Regulatory Elements

Promoter connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to reduce expression of A622 or NBB1 may be constitutive promoters, or tissue-specific, tissue-preferred, cell type-specific, and inducible promoters. Preferred promoters include promoters which are active in root tissues, such as the tobacco RB7promoter (Hsu et al. *Pestic. Sci.* 44:9-19 (1995); U.S. Pat. No. 5,459,252) and promoters that are activated under conditions that result in elevated expression of enzymes involved in nicotine biosynthesis such as the tobacco RD2 promoter (U.S. Pat. No. 5,837,876), PMT promoters (Shoji T. et al., *Plant Cell*

*Physiol,* 41:831-839 (2000b); WO 2002/038588) or an A622 promoter (Shoji T. et al., *Plant Mol Biol,* 50:427-440 (2002)).

The vectors of the invention may also contain termination sequences, which are positioned downstream of the nucleic acid molecules of the invention, such that transcription of mRNA is terminated, and polyA sequences added. Exemplary of such terminators are the cauliflower mosaic virus (CaMV) 35S terminator and the nopaline synthase gene (Tnos) terminator. The expression vector also may contain enhancers, start codons, splicing signal sequences, and targeting sequences.

Expression vectors of the invention may also contain a selection marker by which transformed plant cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or plant cell containing the marker. Usually, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phospho-ribosyltransferase, glyphosate and glufosinate resistance, and amino-glycoside 3'-O-phosphotranserase (kanamycin, neomycin and G418 resistance). These markers include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., *EMBO J.* 9: 2519-2523 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of a plant to suppress nicotinic alkaloid synthesis via introducing a polynucleotide sequence that down-regulates expression of a gene, such as A622 and NBB1, that regulates nicotinic alkaloid synthesis. The result is a plant having reduced nicotinic alkaloid levels.

In this description, "plant" denotes any nicotinic alkaloid containing plant material that can be genetically manipulated, including but not limited to differentiated or undifferentiated plant cells, protosomes, whole plants, plant tissues, or plant organs, or any component of a plant such as a leaf, stem, root, bud, tuber, fruit, rhizome, or the like.

Illustrative plants that can be engineered in accordance with the invention include but are not limited to tobacco, potato, tomato, egg plant, green pepper, and *Atropa belladonna*.

Plant Transformation and Selection

Constructs according to the invention may be used to transform any plant cell, using a suitable transformation technique. Both monocotyledonous and dicotyledonous angiosperm or gymnosperm plant cells may be transformed in various ways known to the art. For example, see Klein et al., *Biotechnology* 4: 583-590 (1993); Bechtold et al., *C. R. Acad. Sci. Paris* 316:1194-1199 (1993); Bent et al., *Mol. Gen. Genet.* 204:383-396 (1986); Paszowski et al., *EMBO J.* 3: 2717-2722 (1984); Sagi et al., *Plant Cell Rep.* 13: 262-266 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433:629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation (Lorz et al., *Mol. Genet.* 199: 179-182 (1985)), and other methods known to the art. If a selection marker, such as kanamycin resistance, is employed, it makes it easier to determine which cells have been successfully transformed.

The *Agrobacterium* transformation methods discussed above are known to be useful for transforming dicots. Additionally, de la Pena et al., *Nature* 325: 274-276 (1987), Rhodes et al., *Science* 240: 204-207 (1988), and Shimamato et al., *Nature* 328: 274-276 (1989) have transformed cereal monocots using *Agrobacterium*. Also see Bechtold et al., *C.R. Acad. Sci. Paris* 316 (1994), illustrating vacuum infiltration for *Agrobacterium*-mediated transformation.

For the purposes of this description, a plant or plant cell may be transformed with a plasmid comprising one or more sequences, each operably linked to a promoter. For example, an illustrative vector may comprise a QPT sequence operably linked to a promoter. Likewise, the plasmid may comprise a QPT sequence operably linked to a promoter and an A622 sequence operably linked to a promoter. Alternatively, a plant or plant cell may be transformed with more than one plasmid. For example, a plant or plant cell may be transformed with a first plasmid comprising a QPT sequence operably linked to a promoter, which is distinct from a second plasmid comprising an A622 or NBB1 sequence. Of course, the first and second plasmids or portions thereof are introduced into the same plant cell Genetically engineered plants of the invention may be produced by conventional breeding. For example, a genetically engineered plant having down-regulated QPT and A622 activity may be produced by crossing a transgenic plant having reduced QPT expression with a transgenic plant having reduced A622 expression. Following successive rounds of crossing and selection, a genetically engineered plant having down-regulated QPT and A622 activity can be selected.

The presence of a protein, polypeptide, or nucleic acid molecule in a particular cell can be measured to determine if, for example, a cell has been successfully transformed or transfected.

Marker genes may be included within pairs of recombination sites recognized by specific recombinases such as cre or flp to facilitate removal of the marker after selection. See U.S. published application No. 2004/0143874.

Transgenic plants without marker genes may be produced using a second plasmid comprising a nucleic acid encoding the marker, distinct from a first plasmid that comprises an A622 or NBB1 sequence. The first and second plasmids or portions thereof are introduced into the same plant cell, such that the selectable marker gene that is transiently expressed, transformed plant cells are identified, and transformed plants are obtained in which the A622 or NBB1 sequence is stably integrated into the genome and the selectable marker gene is not stably integrated. See U. S. published application No. 2003/0221213. The first plasmid that comprises an A622 or NBB1 sequence may optionally be a binary vector with a T-DNA region that is completely made up of nucleic acid sequences present in wild-type non-transgenic *N. tabacum* or sexually compatible *Nicotiana* species.

Plant cells may be transformed with nucleic acid constructs of the present invention without the use of a selectable or visible marker and transgenic plant tissue and transgenic regenerated plants may be identified by detecting the presence of the introduced construct by PCR or other methods of detection of specific nucleic acid sequences. Identification of transformed plant cells may be facilitated by recognition of differences in the growth rate or a morphological feature of said transformed plant cell compared to the growth rate or a morphological feature of a non-transformed plant cell that is cultured under similar conditions (see WO 2004/076625).

Methods of regenerating a transgenic plant from a transformed cell or culture vary according to the plant species but are based on known methodology. For example, methods for regenerating of transgenic tobacco plants are well-known.

For the purposes of the present description, genetically engineered plants are selected that have down-regulated expression of at least one of A622 and NBB1. Additionally, the inventive genetically engineered plants may have down-regulated expression of a nicotine biosynthesis gene, such as QPT or PMT, and at least one of A622 and NBB1.

Nicotine serves as a natural pesticide which helps protect tobacco plants from damage by pests and susceptibility of conventionally bred or transgenic low-nicotine tobacco to insect damage has been reported to increase. Legg, P. D., et al., *Can. J. Cyto.*, 13:287-291 (1971); Voelckel, C., et al., *Chemoecology* 11:121-126 (2001); Steppuhn, A., et al., *PLoS Biol*, 2(8): e217: 1074-1080 (2004). It may therefore be desirable to additionally transform reduced-nicotine plants produced by the present methods with a transgene that will confer additional insect protection, such as gene encoding a Bt insecticidal protein, proteinase inhibitor, or biotin-binding protein. A transgene conferring additional insect protection may be introduced by crossing a transgenic reduced-nicotine plant with a second transgenic plant containing a gene encoding an insect resistance protein.

Quantifying Nicotinic Alkaloid Content

Transgenic plants of the invention are characterized by decreased nicotinic alkaloid content. Decreased nicotinic alkaloid content in the genetically engineered plant is preferably achieved via decreased expression of a nicotine biosynthesis pathway gene, such as A622 or NBB1.

In describing a plant of the invention, the phrase "reduced-nicotine or nicotinic alkaloid content" refers to a quantitative reduction in the amount of nicotinic alkaloid in the plant when compared with a non-transformed control plant. A quantitative decrease in nicotinic alkaloid levels can be assayed by several methods, as for example by quantification based on gas-liquid chromatography, high performance liquid chromatography, radio-immunoassays, and enzyme-linked immunosorbent assays. In the present invention, nicotinic alkaloid levels were measured by gas-liquid chromatography equipped with a capillary column and an FID detector, as described in Hibi, N. et al., *Plant Physiology* 100: 826-835 (1992).

Reduced-Nicotinic-Alkaloid Products

The present invention provides a transgenic plant having reduced-nicotinic-alkaloid levels. For example, the instant invention contemplates reducing nicotine levels by suppressing at least one of A622 and NBB1 expression. Following selection of a transgenic plant having suppressed A622 or NBB1 expression and reduced-nicotine content, a variety of products may be made from such a plant.

Because the invention provides a method for reducing alkaloids, TSNAs may also be reduced because there is a significant, positive correlation between alkaloid content in tobacco and TSNA accumulation. For example, a significant correlation coefficient between anatabine and NAT was 0.76. Djordjevic et al., *J. Agric. Food Chem.*, 37: 752-756 (1989). TSNAs are a class of carcinogens that are predominantly formed in tobacco during curing, processing, and smoking. However, TSNAs are present in small quantities in growing tobacco plants or fresh cut tobacco. Hecht & Hoffman, *J. Natl. Cancer Inst.* 58, 1841-4 (1977); Wiernik et al., *Recent Adv. Tob. Sci*, 21: 39-80 (1995). Nitrosamines, containing the organic functional group, N—N=O, are formed from the facile addition of an N=O group by a nitrosating agent to a nitrogen of a secondary or tertiary amine. This particular class of carcinogens is found only in tobacco although they could potentially occur in other nicotine-containing products.

TSNAs are considered to be among the most prominent carcinogens in cigarette smoke and their carcinogenic properties are well documented. See Hecht, S. *Mutat. Res.* 424:127-42 (1999); Hecht, S. *Toxicol.* 11, 559-603 (1998); Hecht, S., et al., *Cancer Surv.* 8, 273-294 (1989). TSNAs have been cited as causes of oral cancer, esophageal cancer, pancreatic cancer, and lung cancer (Hecht & Hoffman, *IARC Sci. Publ.* 54-61 (1991)). In particular, TSNAs have been implicated as the causative agent in the dramatic rise of adenocarcinoma associated with cigarette smoking and lung cancer (Hoffmann et al., *Crit. Rev. Toxicol.* 26, 199-211 (1996)).

The four TSNAs considered to be the most important by levels of exposure and carcinogenic potency and reported to be possibly carcinogenic to humans are N'-nitrosonornicotine (NNN), 4-methylnitrosoamino-1-(3-pyridyl)-1-butanone (NNK), N'-nitrosoanatabine (NAT) and N'-nitrosoanabasine (NAB) Reviewed in *IARC monographs on the evaluation of the carcinogenic risk of chemical to humans.* Lyon (France) Vol 37, pp. 205-208 (1985). These TSNAs are formed by N-nitrosation of nicotine and of the minor *Nicotiana* alkaloids that include nornicotine, anatabine, and anabasine.

The following levels of alkaloid compounds have been reported for mainstream smoke of non-filter cigarettes (measured in μg/cigarette): nicotine: 100-3000, nornicotine: 5-150, anatabine: 5-15, Anabasine: 5-12 (Hoffmann et al., *Chem. Res. Toxicol.* 14:7:767-790 (2000)). Mainstream smoke of U.S. cigarettes, with or without filter tips, contain (measured in ng/cigarette): 9-180 ng NNK, 50-500 ng NNN, 3-25 ng NAB and 55-300 ng NAT. Hoffmann, et al., *J. Toxicol. Environ. Health* 41:1-52 (1994). It is important to note that the levels of these TSNAs in sidestream smoke are 5-10 fold above those in mainstream smoke. Hoffmann, et al (1994).

Xie et al. (2004) reported that Vector 21-41, which is a GE reduced-nicotine tobacco by the down-regulation of QPT, has a total alkaloid level of about 2300 ppm, which is less than 10 percent of the wild-type tobacco. Mainstream smoke from the Vector 21-41 cigarettes had less than 10 percent of NNN, NAT, NAB, and NNK compared to such levels of a standard full flavor cigarette produced from wild-type tobacco.

The strategy for reducing TSNAs by reducing the corresponding tobacco alkaloid precursors is currently the main focus of agricultural tobacco research. Siminszky et al., *Proc. Nat. Acad. Sci. USA* 102(41) 14919-14924 (2005). Thus, to reduce formation of all TSNAs there is an urgent need to reduce the precursor nicotinic alkaloids as much as possible by genetic engineering.

Among others, U.S. Pat. Nos. 5,803,081, 6,135,121, 6,805,134, 6,907,887 and 6,959,712 and U.S. Published Application Nos. 2005/0034365 and 2005/0072047 discuss methods to reduce tobacco-specific nitrosamines (TSNAs).

A reduced-nicotine tobacco product may be in the form of leaf tobacco, shredded tobacco, cut tobacco and tobacco fractions. A reduced-nicotine tobacco product may include cigarette tobacco, cigar tobacco, snuff, chewing tobacco, pipe tobacco, and cigarettes made from GE reduced-nicotine tobacco for use in smoking cessation.

Reduced-nicotine tobacco may also be used to produce reconstituted tobacco (Recon). Recon is produced from tobacco stems and/or smaller leaf particles by a process that closely resembles typical paper making. This process entails processing the various tobacco portions that are to be made into Recon and cutting the tobacco into a size and shape that resembles cut rag tobacco made from whole leaf tobacco. This cut recon then gets mixed with cut-rag tobacco and is ready for cigarette making.

In addition to traditional tobacco products, such as cigarette and cigar tobacco, reduced-nicotine tobacco can be used as source for protein, fiber, ethanol, and animal feeds. See U.S. published application No. 2002/0197688. For example, reduced-nicotine tobacco may be used as a source of Rubisco (ribulose bisphosphate carboxylase-oxygenase or fraction 1 protein) because unlike other plants, tobacco-derived Rubisco can be readily extracted in crystalline form. With the exception of slightly lower levels of methionine, Rubisco's content of essential amino acids equals or exceeds that of the FAO Provisional Pattern. Ershoff, B. H., et al. *Society for Experimental Biology and Medicine* 157:626-630 (1978); Wildman, S. G. *Photosynthesis Research* 73:243-250 (2002)).

For biofuels to replace a sizable portion of the world's dependence on non-renewable energy sources, co-products, such as Rubisco, are required to help defray the cost of producing this renewable energy. Greene et al. *Growing Energy. How Biofuels Can End America's Oil Dependence*; National Resources Defense Counsel (2004). Thus, the greater reduction in nicotinic alkaloids in tobacco, the greater the likelihood of a successful tobacco biomass system.

Specific examples are presented below of methods for identifying sequences encoding enzymes involved in nicotine, as well as for introducing the target gene to produce plant transformants. They are meant to be exemplary and not as limitations on the present invention.

Figure 2A:
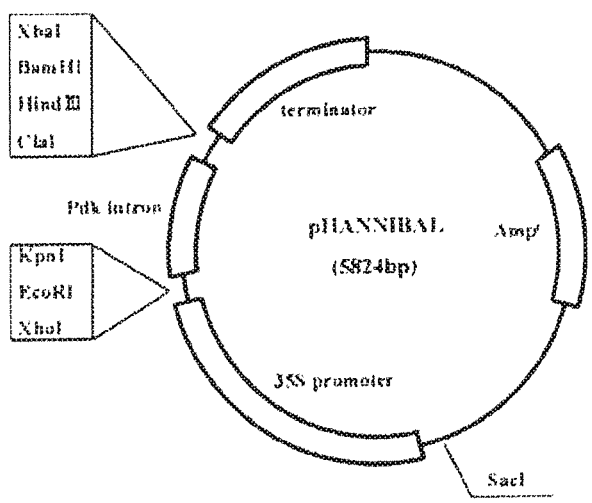
FIG. 2A schematically illustrates pHANNIBAL.
Figure 2B:
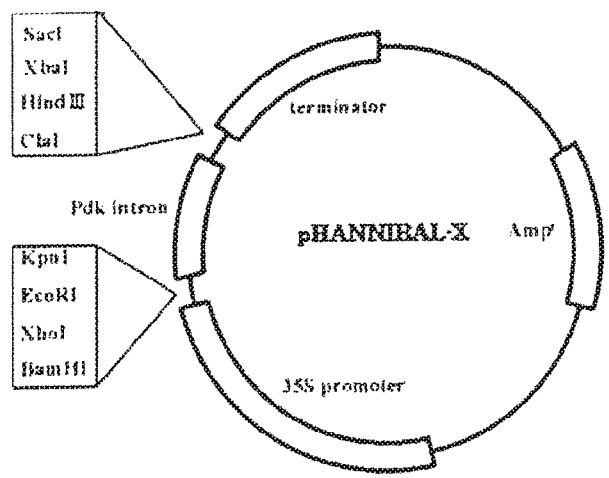
FIG. 2B schematically illustrates pHANNIBAL-X in which the multilinker sites have been modified.

Example 1: Preparation of pRNAi-A622 Vector for Reducing Alkaloid Content by Down-Regulating A622 Expression The plasmid pHANNIBAL, see Wesley et al., *Plant J.* 27: 581-590 (2001), was modified to produce plasmid pHANNIBAL-X as shown in FIG. 2. A SacI restriction site between the ampicillin resistance gene (Amp) and 35S promoter was eliminated by SacI cutting and subsequent DNA blunting and ligation. The multi-cloning sites (MCS) were modified as follows. A Bam H I restriction site was added to the MCS between the promoter and Pdk intron by inserting an adaptor (5' TCGAACGGGATCCCGCCGCTC-GAGCGG) (SEQ ID NO: 5) between the XhoI and EcoRI sites. A Bam H1 site was eliminated from and a Sac I site was inserted into the MCS between the intron and terminator by inserting an adaptor (5' GATCAGCTCTAGAGC-CGAGCTCGC) (SEQ ID NO: 6) between the BamHI and XbaI sites.

Figure 3:
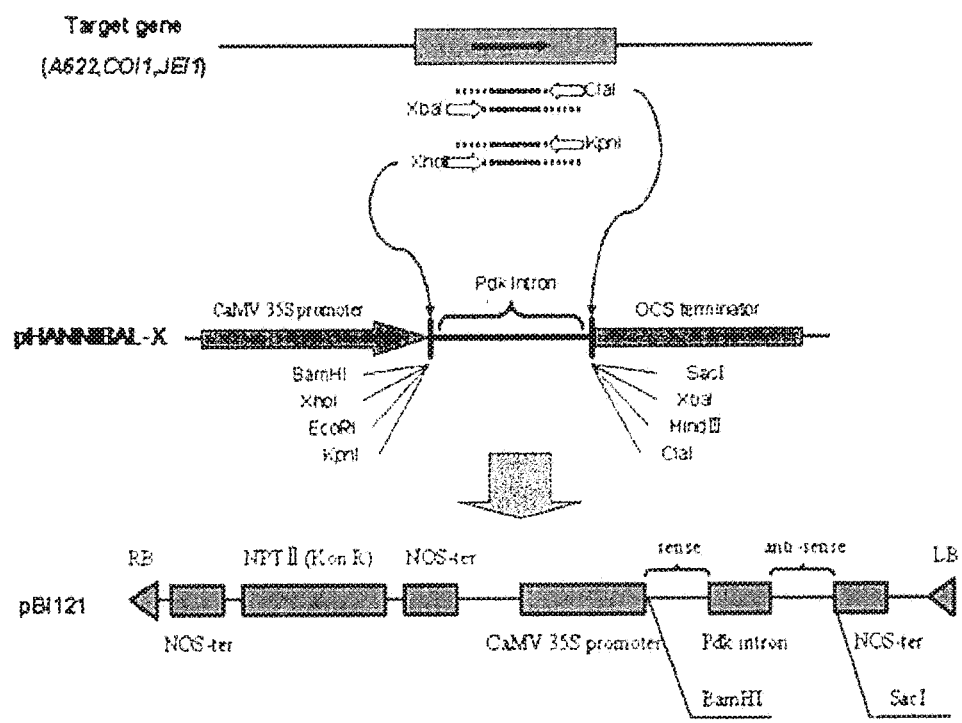
FIG. 3 depicts the scheme for preparing a plant RNAi binary vector using the modified pHANNIBAL-X as an intermediate plasmid.

A plant RNAi binary vector was prepared using pHANNIBAL-X using the scheme diagramed in FIG. 3, in which distinct "sense" and "antisense" fragments are first obtained by the addition of specific restriction sites to the ends of a segment of the gene of interest, and then the sense and antisense fragments are inserted in the desired orientations in the modified pHANNIBAL-X plasmid.

The DNA segment containing the sense and antisense fragments and the intervening Pdk intron was substituted for the GUS coding region of pBI121 (Wesley et al., 2001) to produce an RNAi binary vector.

The 814 bp-1160 bp region of the A622 cDNA was used as the dsRNA forming region (sense chain, antisense chain). PCR was performed using A622 cDNA cloned in pcDNAII as the template and primers with additional bases encoding the indicated restriction enzyme sites, and the target DNA fragment was collected and TA cloned to a pGEM-T vector.

The sequences of the primers used were:

```
Sense chain A622 F814-XhoI - A622 R1160-KpnI
                                     (SEQ ID NOS 7-8)
A622 F814-XhoI
5' CCGCTCGAGCGGTCAGAGGAAGATATTCTCCA 3'

A622 R1160-KpnI
5' GGGGTACCCCTGGAATAAGACGAAAAATAG 3'

Antisense chain A622 F814-XbaI - A622 R1160-ClaI
                                     (SEQ ID NOS 9-10)
A622 F814-XbaI
5' GCTCTAGAGCTCAGAGGAAGATATTCTCCA 3'

A622 R1160-ClaI
5' CCATCGATGGTGGAATAAGACGAAAAATAG 3'
```

Recombination with the modified pHANNIBAL-X was performed starting with the sense chain followed by the antisense chain. The TA cloned DNA fragments were cut with the appropriate restriction enzymes, collected, and ligated to pHANNIBAL-X which was cut with the same restriction enzymes. The resulting plasmid contains a DNA sequence with inverted repeats of the A622 fragment separated by the Pdk intron.

Figure 4:
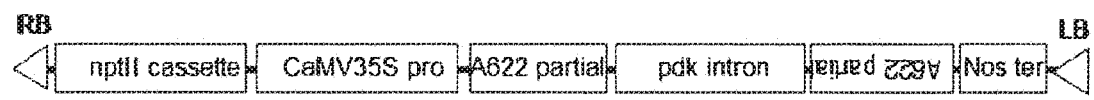
FIG. 4 depicts the T-DNA region of pRNAi-A622.

The RNAi region was excised from the pHANNIBAL-X with the incorporated sense and antisense chains by treating with BamH I and Sac I and ligated to pBI121 from which the GUS coding region had been removed by similar treatment to produce the binary vector pRNAi-A622 for plant transformation, which contains a T-DNA segment (FIG. 4) that contains an nptII selectable marker cassette and the A622 RNAi cassette.

Example 2: Suppression of A622 in Tobacco BY-2 Cells

While tobacco BY-2 cell cultures do not normally synthesize nicotinic alkaloids, methyl jasmonate treatment induces expression of genes for known enzymes in the nicotine biosynthesis pathway and elicits formation of nicotinic alkaloids.

In order to deduce the function of A622, RNAi strain cultured cells were prepared in which mRNA from pRNAi-A622 was expressed in cultured tobacco BY-2 cells to suppress A622.

Agrotransformation

The vector (pRNAi-A622) was transformed into *Agrobacterium tumefaciens* strain EH105, which was used to transform tobacco BY-2 cells. The methods for infecting and selecting the tobacco BY-2 cells were as follows.

Four ml of BY-2 cells which had been cultured for 7 days in 100 ml of modified LS medium, see Imanishi et al., *Plant Mol. Biol.*, 38: 1101-1111 (1998), were subcultured into 100 ml modified LS medium, and cultured for 4 days.

One hundred microliters of *A. tumefaciens* solution, which had been cultured for 1 day in YEB medium, were added to the 4 ml of cells that had been cultured for 4 days, and the two were cultured together for 40 hours in the dark at 27° C.

After culture, the cells were washed twice with modified LS medium to remove the Agrobacteria.

The washed cells were spread on modified LS selection medium containing kanamycin (50 mg/l) and carbenicillin (250 mg/l), and transformed cells were selected.

After having been cultured for about 2 weeks in the dark at 27° C., the transformed cells were transferred to a fresh modified LS selection medium, and cultured in the dark for 1 week at 27° C.

The transformed cells were then grown in a suspension culture in the dark at 27° C. for 1 week in 30 ml of liquid modified LS medium.

1 ml of the cultured transformed cells was subcultured to 100 ml of modified LS medium. The transformed cells were subcultured every 7 days in the same way as wild-type cells.

Alkaloid Synthesis 10 ml each of transformed BY-2 cells which had been cultured for 7 days and cultured tobacco cells which had been transformed using a green fluorescent protein (GFP) expression vector as the control were washed twice with modified LS medium containing no 2,4-D, and, after addition of modified LS medium containing no 2,4-D to a total of 100 ml, were suspension cultured at 27° C. for 12 hours.

After addition of 100 μl of methyljasmonate (MeJa) which had been diluted to 50 μM with DMSO, the cells were suspension cultured for 48 hours at 27° C.

Jasmonate treated cells were filtered, collected, and freeze dried. Sulfuric acid, 3 ml of 0.1 N, was added to 50 mg of the freeze-dried sample. The mixture was sonicated for 15 minutes, and filtered. A 28% ammonium solution was added to 1 ml of the filtrate, and centrifuged for 10 minutes at 15000 rpm.

One ml of the supernatant was added to an Extrelut-1 column (Merck) and let sit for 5 minutes. This was eluted with 6 ml of chloroform. The eluate was then dried under reduced pressure at 37° C. with an evaporator (Taitec Concentrator TC-8).

The dried sample was dissolved in 50 μl of ethanol solution containing 0.1% dodecane. A gas chromatograph (GC-14B) equipped with a capillary column and an FID detector was used to analyze the samples. A RESTEC Rtx-5Amine column (Restec) was used as the capillary column. The column temperature was maintained at 100° C. for 10 min, elevated to 150° C. at 25° C./min, held at 150° C. for 1 min, elevated to 170° C. at 1° C./min, held at 170° C. for 2 min, elevated to 300° C. at 30° C./min, and then held at 300° C. for 10 min. Injection and detector temperature was 300° C. One μl of each sample was injected, and nicotinic alkaloids were quantified by the internal standard method.

Figure 5:
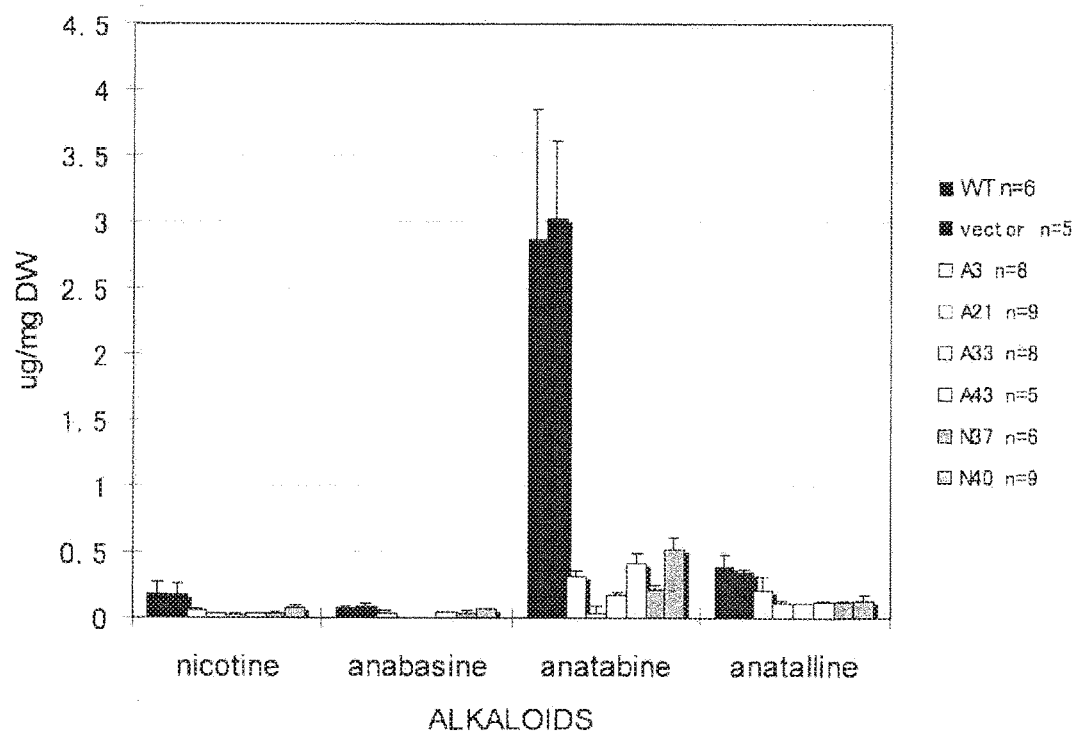
FIG. 5 depicts nicotinic alkaloid accumulation in BY-2 cells, A662-silenced BY-2 cells, and NBB1-silenced BY-2 cells. Abbreviations: WT—wild type, nontransformed cells; vector—cells transformed with marker only; A3, A21, A33, A43—cells transformed with a construct for suppression of A622; N37, N40—cells transformed with a construct for suppression of NBB1.

As shown in FIG. 5, in the transgenic BY-2 lines in which the A622 gene expression was suppressed by RNAi (A3, A21 A33 and A43 lines), jasmonate elicitation did not result in high accumulation of anatabine (the major alkaloid in elicited cultured cells), anatalline, nicotine, or anabasine, compared with control cell lines.

RNA Expression

To determine whether the reduction of alkaloid accumulation in the A622-RNAi lines is specifically related to reduction of A622 expression, rather than an indirect effect on the levels of expression of genes for known enzymes in the nicotine biosynthesis pathway, the levels of expression of A622 and other genes was measured in methyl jasmonate treated lines, transgenic lines, and control lines.

Total RNAs were isolated from wild-type and transgenic BY-2 cell lines which were treated with 50 μM MeJA for 48 h. RNA levels of specific genes were determined by RT-PCR. RNA was extracted using RNeasy Plant mini kit (Qiagen) according to the manufacture's instructions. cDNA was synthesized using random hexamers and SuperScript First-Strand Synthesis System for RT-PCR (Invitrogen). RT-PCR was performed with 5 ng of the cDNA as a template using a TaKaRa ExTaq (Takara Bio) under the following conditions: for detection of A622, NBB1, AO, QS, QPT, ODC, 22 cycles of 94° C. for 30 sec, 57° C. for 30 sec, and 72° C. for 30 sec, for detection of PMT, 24 cycles of 94° C. for 1 min, 52° C. for 30 sec, and 72° C. for 1 min.

```
A622 primers:
                                     (SEQ ID NOS 11-12)
A622-07F      5' ATGGTTGTATCAGAGAAAAG

A622-05R      5' CCTTCTGCCTCTATCATCCTCCTG

NBB1 primers:
                                     (SEQ ID NOS 13-14)
NBB1-01F      5'ATGTTTCCGCTCATAATTCTG

NBB1-1365     5'TCTTCGCCCATGGCTTTTCGGTCT

AO primers:
                                     (SEQ ID NOS 15-16)
AO RT-1       5' CAAAACCAGATCGCTTGGTC

AO RT-2       5' CACAGCACTTACACCACCTT

QS primers:
                                     (SEQ ID NOS 17-18)
QS RT-1       5' CGGTGGAGCAAAAGTAAGTG

QS RT-2       5' GAAACGGAACAATCAAAGCA

QPT primers:
                                     (SEQ ID NOS 19-20)
QPT RT-1      5' TCACTGCTACAGTGCATCCT

QPT RT-2      5' TTAGAGCTTTGCCGACACCT
```

```
-continued
ODC primers:
                                 (SEQ ID NOS 21-22)
    ODC RT-1       5' CGTCTCATTCCACATCGGTAGC

ODC RT-2       5' GGTGAGTAACAATGGCGGAAGT

PMT primers:
                                 (SEQ ID NOS 23-24)
    PMT RT-1       5' GCCATGATAATGGCAACGAG

PMT RT-2       5' TTAGCAGCGAGATAAGGGAA
```

Figure 6:
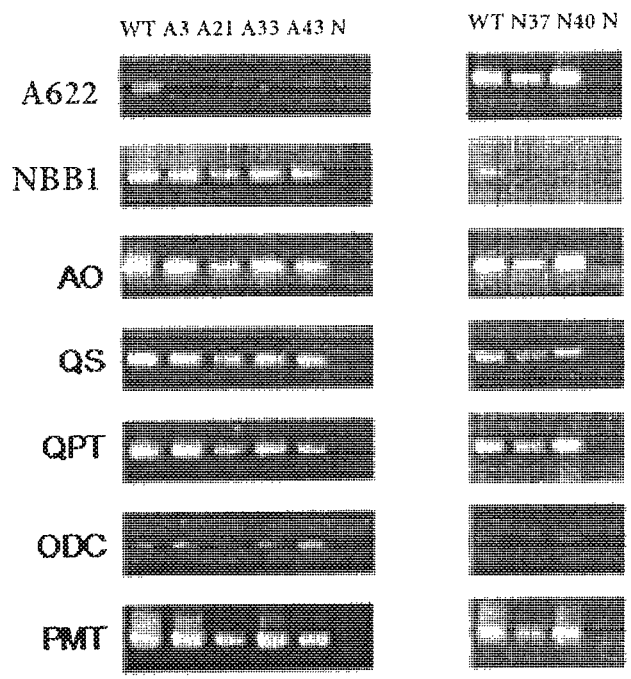
FIG. 6 depicts expression of A622, NBB1, and genes for known enzymes in the nicotine biosynthesis pathway in wild-type BY-2 cells, A622-silenced BY-2 cells, and NBB1-silenced BY-2 cells. A3, A21, A33 and A43 are A622-silenced lines; N37 and N40 are NBB1-silenced lines. WT is a non-transformed control. N is a negative control.

As shown in FIG. 6, A622 is not induced in A622-silenced lines. Other genes for known nicotine biosynthetic pathway enzymes are induced. These results provide evidence that A622 is included in the nicotinic alkaloid biosynthesis pathway, and demonstrate that the nicotinic alkaloid content and particularly the nicotine content of plant cells having nicotine-producing ability can be reduced by down-regulating A622 expression.

Example 3: Construction of an Inducible 4622 RNAi Vector

Constitutive suppression of A622 expression in tobacco hairy roots significantly inhibited root growth, precluding analysis of nicotinic alkaloids. To circumvent this, an estradiol-inducible gene expression system (XVE system) was developed. The XVE system produces RNAi hairpin molecules and target genes are suppressed only after addition of an inducer (beta-estradiol) into the culture medium.

The RNAi region containing A622 sense and antisense DNA fragments was excised from the pHANNIBAL-X plasmid with Xho I and Xba I, and ligated into pBluescript KS which had been digested with Xho I and Xba I. The RNAi region was then excised with Xho I and Spe I, and was subcloned between the XhoI and SpeI sites in the MCS of the XVE vector pER8 (Zuo J. et al, *Plant J.,* 24: 265-273 (2000)) to produce the binary vector pXVE-A622RNAi.

Figure 7:
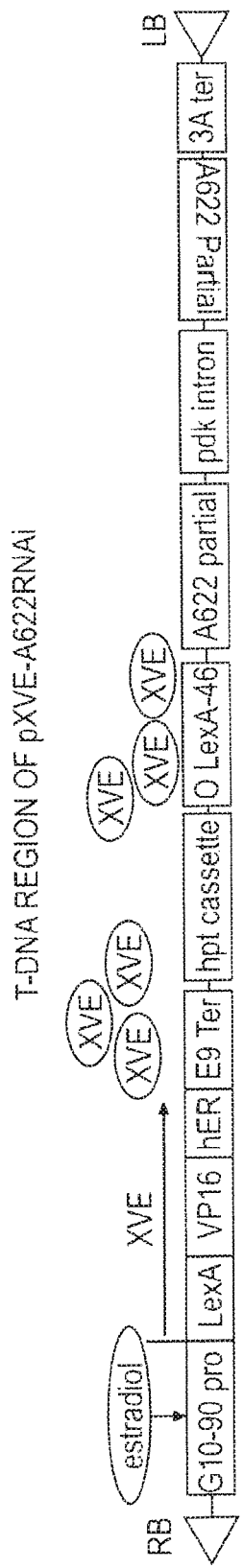
FIG. 7 depicts the T-DNA region of the inducible A622 expression vector pXVE-A622RNAi.

The T-DNA region of pXVE-A622RNAi (See FIG. 7) contains a cassette for estradiol-inducible expression of the chimeric transcription factor XVE, an hpt selectable marker cassette, and a cassette in which expression of the A622 RNAi is under the control of the LexA-46 promoter, which is activated by XVE.

Example 4: Suppression of A622 in Tobacco Hairy Roots

The binary vector pXVE-A622RNAi was introduced to *Agrobacterium rhizogenes* strain 15834 by electroporation. *N. tabacum* cv. Petit Havana SR1 plants were transformed by *A. rhizogenes* using a leaf-disc method, as described by Kanegae et al., *Plant Physiol.* 105(2):483-90. (1994). Hygromycin resistance (15 mg/L in B5 medium) was used to select transformed roots. Transgenic hairy roots were grown at 27° C. in the dark.

Figure 8A:
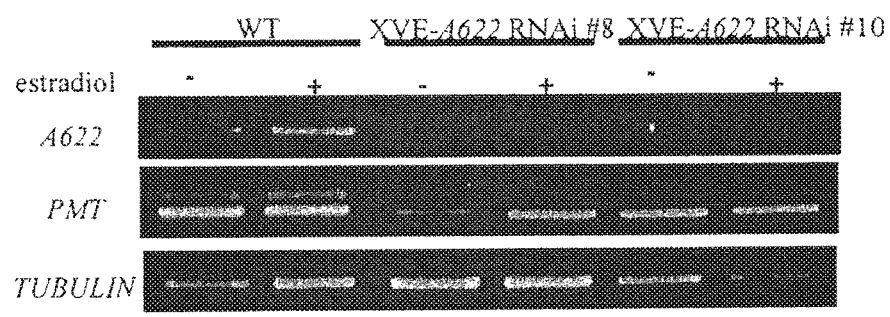
FIG. 8A depicts the specific suppression of A622 in hairy root lines transformed with an inducible A622 suppression construct after inducing suppression with estradiol. Tobacco hairy root lines were cultured with (+) or without (−) addition of estradiol into the liquid culture medium for 4 days, and then roots were harvested and analyzed. WT—non-transformed wild-type line; XVE-A622 RNAi #8 and XVE-A622 RNAi #10-inducible RNAi lines.

Transgenic hairy roots carrying the T-DNA from pXVE-A622RNAi were grown in the B5 medium for 10 days and then gene silencing was induced by addition of 17-beta-estradiol (2 µM) for 4 days. RT-PCR analysis showed that A622 expression was efficiently suppressed in tobacco hairy root lines A8 and A10 transformed with the estradiol-inducible A622 suppression construct after the estradiol addition. See FIG. 8A.

Total RNA was extracted from hairy roots by using RNeasy Plant mini kit (Qiagen). cDNA was synthesized by using random hexamers and SuperScript First-Strand Synthesis System for RT-PCR (Invitrogen). RT-PCR was carried with 2.5 ng of the cDNA as a template using a TaKaRa ExTaq (Takara Bio) under the following conditions: for detection of A622, 22 cycles of 94° C. for 30 sec, 57° C. for 30 sec, and 72° C. for 30 sec; for detection of α-tubulin, 24 cycles of 94° C. for 1 min, 52° C. for 30 sec, and 72° C. for 1 min.

```
Primers for A622 detection;
                                 (SEQ ID NOS 11-12)
    A622-07F       5' ATGGTTGTATCAGAGAAAAG

A622-05R       5' CCTTCTGCCTCTATCATCCTCCTG

Primers for α-tubulin detection;
                                 (SEQ ID NOS 25-26)
    Tub RT-1       5' AGTTGGAGGAGGTGATGATG Tub RT-2       5' TATGTGGGTCGCTCAATGTC
```

Figure 8B:
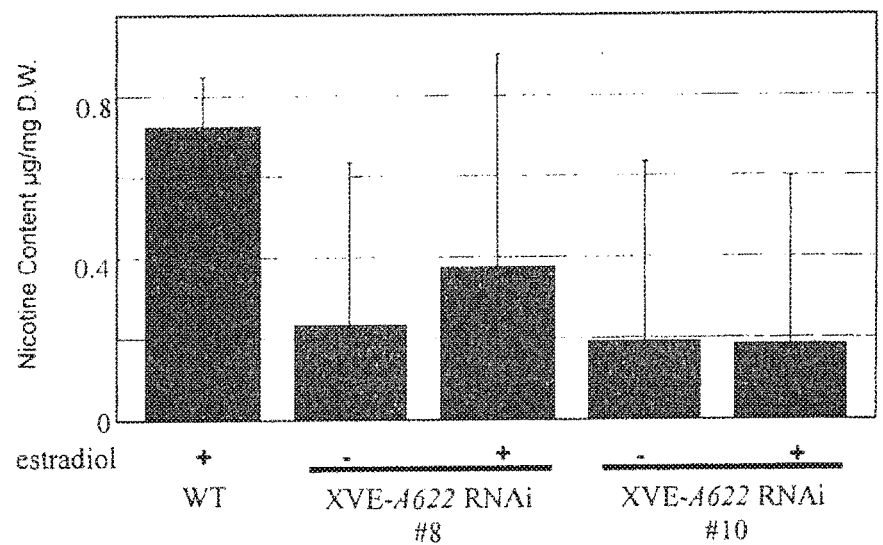
FIG. 8B illustrates reduced-nicotine content in hairy root lines transformed with an inducible A622 suppression construct after inducing suppression with estradiol. Tobacco hairy root lines were cultured with (+) or without (−) addition of estradiol into the liquid culture medium for 4 days, and then roots were harvested and analyzed. WT—non-transformed wild-type line; XVE-A622 RNAi #8 and XVE-A622 RNAi #10-inducible RNAi lines.

Nicotine contents were measured in hairy root lines transformed with an inducible A622 suppression construct without (−) and after induction of suppression with estradiol (+). The RT-PCR graph in FIG. 8B shows that A622 expression was already partially suppressed before estradiol induction. This is especially true with the #8 line. Nicotine contents varied among the A622 suppressed lines but were lower in the A622 suppressed lines than in the wild-type hairy roots.

Example 5: Identification of NBB1 as a Gene Regulated by the NIC Loci

A cDNA micro-array prepared from a *Nicotiana sylvestris*-derived cDNA library (Katoh et al., *Proc. Japan Acad.,* Vol. 79, Ser. B, No. 6, pp. 151-154 (2003)) was used to search for novel genes which are controlled by the nicotine biosynthesis regulatory NIC loci.

*N. sylvestris* cDNAs were amplified by PCR and spotted onto mirror-coated slides (type 7 star, Amersham) by using Amersham Lucidea array spotter. DNA was immobilized on the slide surface by UV crosslinking (120 mJ/m$^2$). *N. tabacum* Burley 21 plantlets (WT and nic1nic2) were grown on half-strength B5 medium supplemented with 1.5% (W/V) sucrose and 0.35% (W/V) gellan gum (Wako) in Agripot containers (Kirin).

Roots of eight-week-old plantlets were harvested, immediately frozen with liquid nitrogen, and kept at −80° C. until use. Total RNA was isolated using Plant RNeasy Mini kit (Qiagen) from the frozen roots, and mRNA was purified using GenElute mRNA Miniprep kit (Sigma). cDNA was synthesized from 0.4 g of the purified mRNA by using LabelStar Array Kit (Qiagen) in the presence of Cy3 or Cy5-dCTP (Amersham). cDNA hybridization to the microarray slides and post-hybridization washes were performed using a *Lucida* Pro hybrid-machine (Amersham). Microarrays were scanned using an FLA-8000 scanner (Fujifilm). Acquired array images were quantified for signal intensity with ArrayGauge software (Fujifilm). cDNA probes from wild type and nic1nic2 tobacco were labeled with Cy3 and Cy5 in reciprocal pair-wise combinations. Hybridization signals were normalized by accounting for the total signal intensity of dyes. cDNA clones which hybridized to wild-type probes more than twice as strongly compared to nic1nic2 probes were identified, and these included NBB1.

Full-length NBB1 cDNA was obtained by 5'- and 3'-RACE from total RNA of *N. tabacum* by using a SMART RACE cDNA Amplification Kit (Clontech).

The nucleotide sequence of the NBB1 cDNA insert was determined on both strands using an ABI PRISM® 3100 Genetic Analyzer (Applied Biosystems) and a BigDye® Terminator v3.1 Cycle Sequencing Kit (Applied Biosystems). The nucleotide sequence of NBB1 is set forth in SEQ ID NO: 3. The amino acid sequence encoded by the nucleotide sequence is set forth in SEQ ID NO: 4. The protein sequence includes a FAD-binding motif. A putative vacuolar signal peptide is located at N-terminus.

Example 6: Characterization of NBB1

NBB1 expression was investigated in tobacco plants by Northern blot analysis.

RNA was extracted from plant bodies which had been treated with methyljasmonate vapor, using Nicotiana tabacum cv. Burley 21 (abbreviated below as WT) and mutants nic1, nic2 and nic1 nic2 having mutations introduced in the Burley 21 background. Cultivation was in a sterile sealed environment, and the plants were raised for 2 months at 25° C. with 150 t mole photons/m$^2$ of light (16 h light, 8 h dark) on ½×B5 medium (3% sucrose, 0.3% gellan gum). Methyl jasmonate treatment was accomplished by adding 0.5 mL of 100 μM methyl jasmonate to an Agripot container (Kirin, Tokyo) with a solid medium capacity of 80 cm$^3$ and a gas capacity of 250 cm$^3$ containing the plants. The treatment times were set at 0 h and 24 h. The root parts and leaf parts ($2^{nd}$ through $6^{th}$ leaves from a plant body with a total of 7 to 10 leaves) were collected from the plant bodies and immediately stored frozen using liquid nitrogen.

RNA was extracted using an RNeasy Midi Kit (Qiagen) according to the manufacturer's protocol. However, polyvinyl pyrrolidine was added to a concentration of 1% to the RLT. The column operation was performed twice to increase the purity of the RNA.

RNA blotting was carried out according to the ordinary methods given by Sambrook and Russell (Sambrook, J. et al., Molecular Cloning, Cold Spring Harbor Laboratory, Chapter 7 (2001)).

The sequence fragment from 1278 bp through the end (1759 bp) of the NBB1 nucleotide sequence (SEQ ID NO: 3) was used as the probe template. The template was prepared by amplification from the cDNA clone using PCR using the following primers:

```
                                (SEQ ID NOS 27-28)
    primer 1: GGAAAACTAACAACGGAATCTCT primer 2: GATCAAGCTATTGCTTTCCCT
```

The probe was labeled with $^{32}$P using a Bcabest labeling kit (Takara) according to the manufacturer's instructions. Hybridization was accomplished using ULTRAhyb (Ambion) as the buffer according to the manufacturer's protocol.

PMT probe was prepared from a PMT sequence cloned into a pcDNAII vector in E. coli (Hibi et al., 1994). The plasmid was extracted and purified from the E. coli using a QIAprep Spin Miniprep Kit (Qiagen), treated with the restriction enzymes XbaI and HindIII by ordinary methods, and run through agarose gel electrophoresis, and about 1.5 kb DNA fragments were collected. A QIAquick Gel Extraction Kit (Qiagen) was used for collection. The collected DNA fragments were $^{32}$P labeled by the same methods used for the NBB1 probe, and hybridized. The results are shown in FIG. 9.

Figure 9:
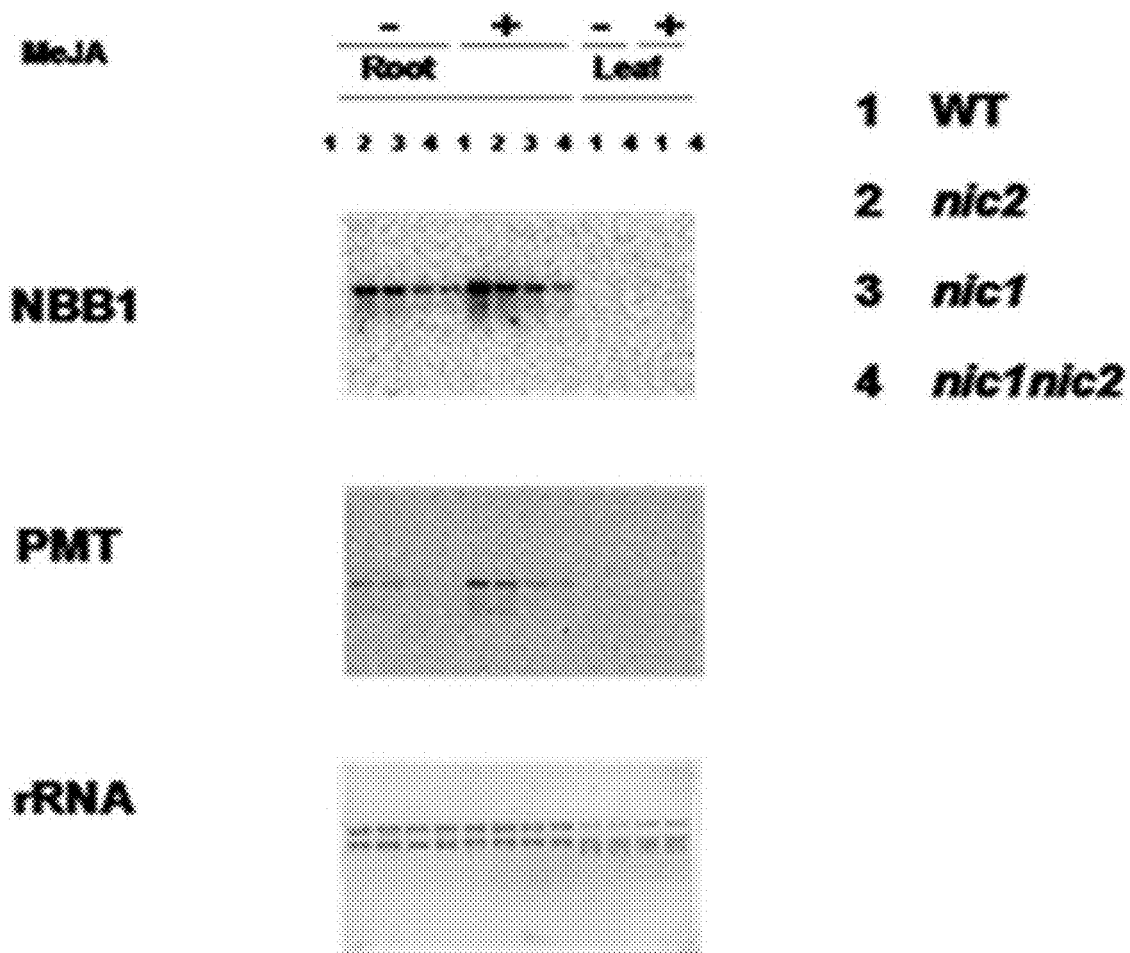
FIG. 9 depicts RNA blot analysis of NBB1 expression and PMT expression in root and leaf tissue of wild type tobacco and nic1, nic2, and nic1nic2 mutants.

As FIG. 9 clearly shows, NBB1 and PMT have the same pattern of expression in tobacco plants. Evidence that NBB1 is involved in nicotine biosynthesis is that, like PMT and A622, NBB1 is under the control of the NIC genes, and it exhibits a similar pattern of expression to PMT and A622.

Example 7: Phylogenetic Analysis of NBB1

NBB1 polypeptide has 25% identity and 60% homology to the Eschscholzia californica berberine bridge enzyme (BBE). (Dittrich H. et al., Proc. Natl. Acad. Sci. USA, Vol. 88, 9969-9973 (1991)). An alignment of the NBB1 polypeptide with EcBBE is shown in FIG. 10.

A phylogenetic tree was constructed using the sequences of NBB1 polypeptide and plant BBE-like polypeptides (based on Carter and Thornburg, Plant Physiol. 134, 460-469 (2004). The phylogenetic analysis was performed using neighbor-joining method with the CLUSTAL W program. Numbers indicate bootstrap values from 1,000 replicates. The sequences used were: EcBBE, California poppy BBE (GenBank accession no. AF005655); PsBBE, opium poppy (Papaver somniferum) probable reticuline oxidase (AF025430); BsBBE, barberry (Berberis stolonifera) BBE (AF049347); VuCPRD2, cowpea (Vigna unguiculata) drought-induced protein (AB056448); NspNEC5, Nicotiana sp. Nectarin V (AF503441/AF503442); HaCHOX, sunflower (Helianthus annuus) carbohydrate oxidase (AF472609); LsCHOX, lettuce (Lactuca sativa) carbohydrate oxidase (AF472608); and 27 Arabidopsis genes (At1g01980, Atg11770, At1g26380, At1g26390, At1g26400, At1g26410, At1g26420, At1g30700, At1g30710, At1g30720, At1g30730, At1g30740, At1g30760, At1g34575, At2g34790, At2g34810, At4g20800, At4g20820, At4g20830, At4g20840, At4g20860, At5g44360, At5g44380, At5g44390, At5g44400, At5g44410, and At5g44440).

Figure 11:
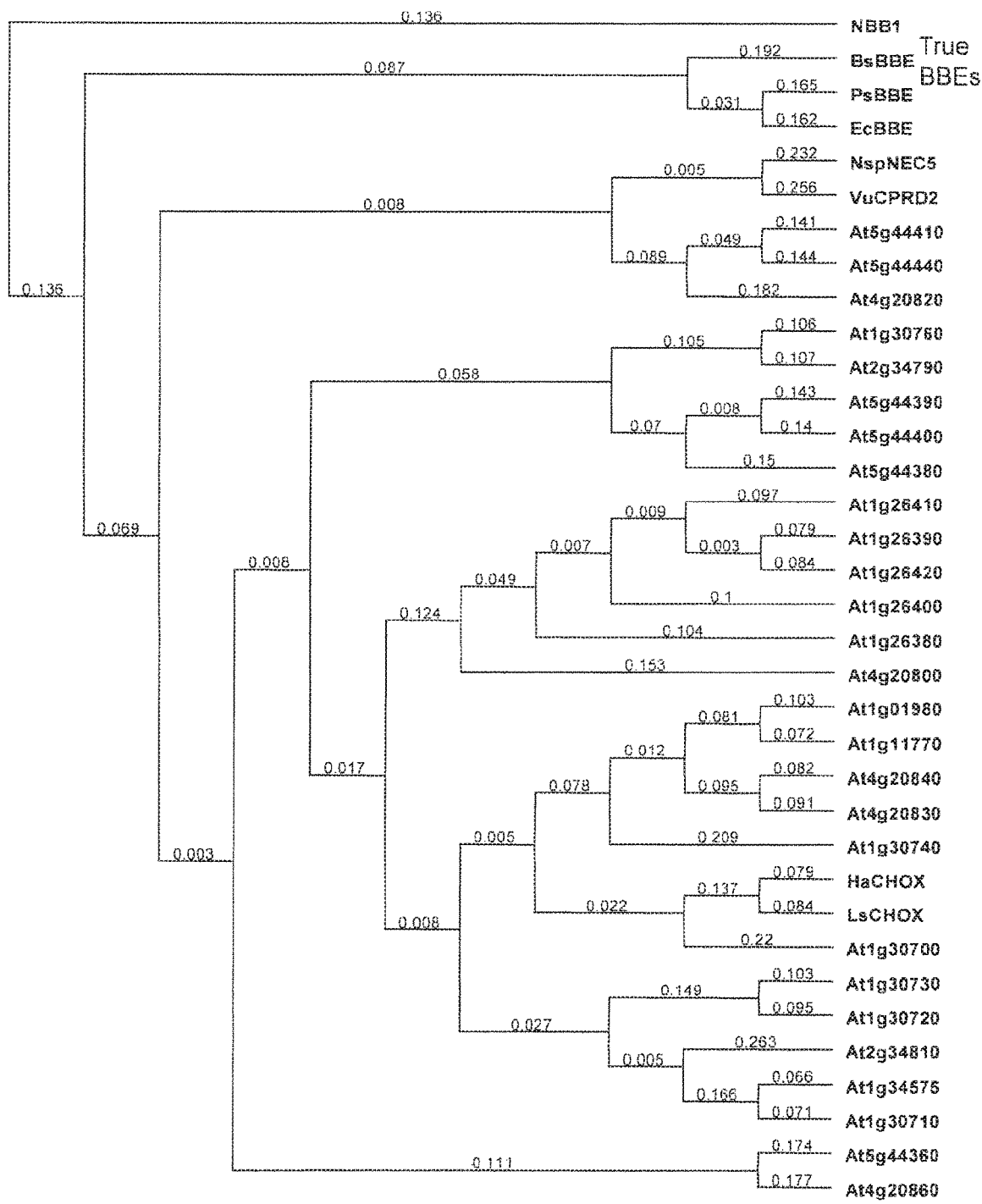
FIG. 11 depicts a phylogenetic tree constructed using NBB1 and plant BBE-like protein sequences.

The results are shown in FIG. 11. The three known BBEs form a separate clade and are underlined and indicated as "True BBEs." The sequence of NBB1 is not highly similar to any of the BBE or BBE-like proteins, and is separated from the other sequences at the base of the tree. The only other BBE like protein described from the genus Nicotiana, nectarin V, a protein described in nectar of the a hybrid ornamental Nicotiana langsdorffii×N. sanderae, Carter and Thornburg (2004), clusters with the cowpea drought-induced protein and several putative BBE-like proteins from Arabidopsis. Because the nectar of the ornamental tobacco lacks alkaloids and nectarin V has glucose oxidase activity, it was concluded that nectarin V is involved in antimicrobial defense in flowers and is not likely to have any role in alkaloid synthesis. Id.

Example 8: Preparation of NBB1 Suppression Construct

The 342-bp DNA fragment of the NBB1 cDNA was amplified by PCR and cloned into pGEM-T vector using the following primers.

```
    Antisense chain
                                (SEQ ID NOS 29-30)
    NBB1-20E-EcoRI
    5' CCGGAATTCGCACAGTGGAATGAAGAGGACG 3'

NBB1-18R-XhoI
    5' CCGCTCGAGGCGTTGAACCAAGCATAGGAGG 3'
```

-continued

Sense chain
(SEQ ID NOS 31-32)
NBB1-16F-ClaI
5' CCATCGATGCACAGTGGAATGAAGAGGACG 3'

NBB1-19R-XbaI
5' GCTCTAGAGCGTTGAACCAAGCATAGGAGG 3'

Resultant PCR products were digested with EcoRI and XhoI for the antisense insertion, and with ClaI and XbaI for sense chain insertion. The sense DNA fragment was subcloned into the pHANNIBAL-X, followed by insertion of the antisense fragment. The resulting plasmid contained a inverted repeat of the NBB1 fragment, separated by the Pdk intron.

Figure 12:
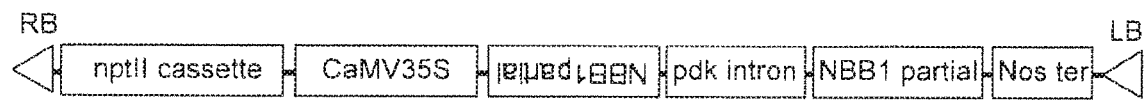
FIG. 12 depicts the T-DNA region of the NBB1 suppression vector pHANNIBAL-NBB1 3'.

The RNAi region was excised from the pHANNIBAL-X with BamH I and Sac I, and ligated into pBI121 to replace the GUS coding region and to produce the binary vector pRNAi-NBB1. The T-DNA region of pHANNIBAL-NBB1 3' (See FIG. 12) contains an nptII selectable marker cassette and cassette for expression of a hairpin RNAi with a double-stranded region corresponding to a 3' fragment of NBB1.

Example 9: NBB1 Suppression in Tobacco BY-2 Cells

Methyl jasmonate treatment of Tobacco BY-2 cells induces NBB1 expression in addition to expression of genes for known enzymes in the nicotine biosynthesis pathway. The effects of NBB1 suppression was tested in BY-2 cells.

The vector pRNAi-NBB1 was introduced into *A. tumefaciens* strain EHA105, which was used to transform tobacco BY-2 cells. BY-2 cells were cultured in 100 ml of modified LS medium. *Agrobacterium tumefaciens* cells (100 µl) in YEB medium were added to 4 ml of BY-2 cells and cultured for 40 hours in the dark at 27° C. After infected tobacco cells were washed twice with modified LS medium, washed tobacco cells were spread on modified LS agar medium containing kanamycin (50 mg/l) and carbenicillin (250 mg/l). After 2 weeks in the dark at 27° C., growing tobacco calluses were transferred to fresh LS selection medium with the same antibiotics, and cultured in the dark at 27° C. for one more week. Growing tobacco cells were transferred to liquid modified LS medium without antibiotics. The transformed tobacco cells were subcultured at a 7-day intervals.

Cultured tobacco cells were cultured with modified LS medium without 2,4-D, at 27° C. for 12 hours. After 100 µl of methyljasmonate (MeJA) dissolved in DMSO was added to 100 mL of the tobacco suspension culture to give a final concentration of 50 µM, tobacco cells were cultured for an additional 48 hours. MeJA-treated cells were filtered, collected, and freeze dried. Sulfuric acid, 3 ml of 0.1 N, was added to 100 mg of the freeze-dried sample. The mixture was sonicated for 15 minutes, and filtered. A 28% ammonium solution was added to 1 ml of the filtrate, and centrifuged for 10 minutes at 15000 rpm. One ml of the supernatant was added to an Extrelut-1 column (Merck) and eluted with 6 ml of chloroform. The eluate was then dried under reduced pressure at 37° C. with an evaporator (Taitec Concentrator TC-8). The dried sample was dissolved in 50 µl of ethanol solution containing 0.1% dodecane. A gas chromatograph (GC-14B) equipped with a capillary column and an FID detector was used to analyze the samples. A RESTEC Rtx-5Amine column (Restec) was used as the capillary column. The column temperature was maintained at 100° C. for 10 min, elevated to 150° C. at 25° C./min, held at 150° C. for 1 min, elevated to 170° C. at 1° C./min, held at 170° C. for 2 min, elevated to 300° C. at 30° C./min, and then held at 300° C. for 10 min. Injection and detector temperature was 300° C. One µl of each sample was injected, and nicotinic alkaloids were quantified by the internal standard method.

Accumulation of nicotinic alkaloids following methyl jasmonate elicitation was greatly reduced in NBB1-suppressed BY-2 cell lines (N37 and N40) compared with wild-type tobacco cells (See FIG. 5).

To determine whether the reduction of alkaloid accumulation in the NBB1-RNAi lines is specifically related to reduction of NBB1 expression, rather than an indirect effect on the levels of expression of genes for known enzymes in the nicotine biosynthesis pathway, the levels of expression of NBB1 and other genes was measured in methyl jasmonate treated lines transgenic and control lines.

Total RNAs were isolated from wild-type and transgenic BY-2 cell lines which had been treated with 50 µM MeJA for 48 h. RNA levels of specific genes were determined by RT-PCR. The results are shown in FIG. 6.

In NBB1-silenced lines induction of NBB1 is not observed, but induction of known genes of the nicotine biosynthetic pathway still occurs, as well as induction of A622. Note also that induction of NBB1 is not affected in A662-suppressed lines.

These results demonstrate that NBB1 reductase is included in the nicotinic alkaloid biosynthesis pathway, and that the nicotinic alkaloid content, and particularly, the nicotine content of plant cells having nicotine-producing ability can be decreased by down-regulating NBB1 expression.

Example 10: NBB1 Suppression in Tobacco Hairy Roots

Tobacco SR-1 hairy roots accumulate nicotine as the major alkaloid. The effect of NBB1 suppression on alkaloid accumulation in hairy roots was studied.

The binary vector pRNAi-NBB1 3' was introduced into *A. rhizogenes* strain 15834 by electroporation. *N. tabacum* cv. Petit Havana SR1 plants were transformed by *A. rhizogenes* using a leaf-disc method, as described above for suppression of A622 in tobacco hairy roots. Hairy roots were selected and cultured and alkaloids were extracted, purified, and analyzed as described above.

Figure 13:
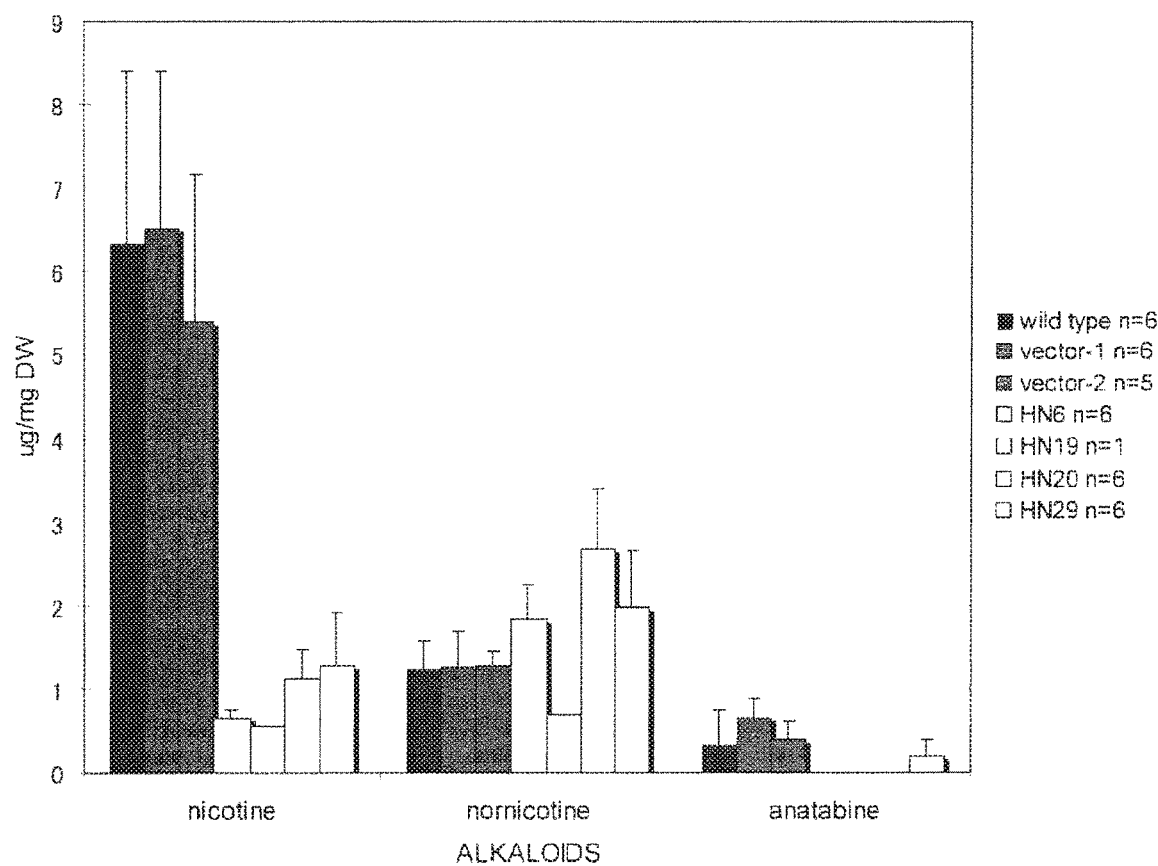
FIG. 13 depicts the reduction of nicotinic alkaloid synthesis in NBB1-suppressed tobacco hairy roots. Wild type—hairy root line produced by transformation with wild-type *A. rhizogenes*; vector 1 and vector 2—hairy root lines produced by transformation with a vector without NBB1 sequences; HN6, HN19, HN20, HN29—hairy root lines produced by transformation with the NBB1 suppression vector pRNAi-NBB1 3'.

When NBB1 expression was suppressed by RNAi, transgenic root lines (HN6, HN19, HN20 and HN29) contained highly reduced levels of nicotine compared with the control cell line, as well as reduced levels of anatabine (See FIG. 13).

Figure 14:
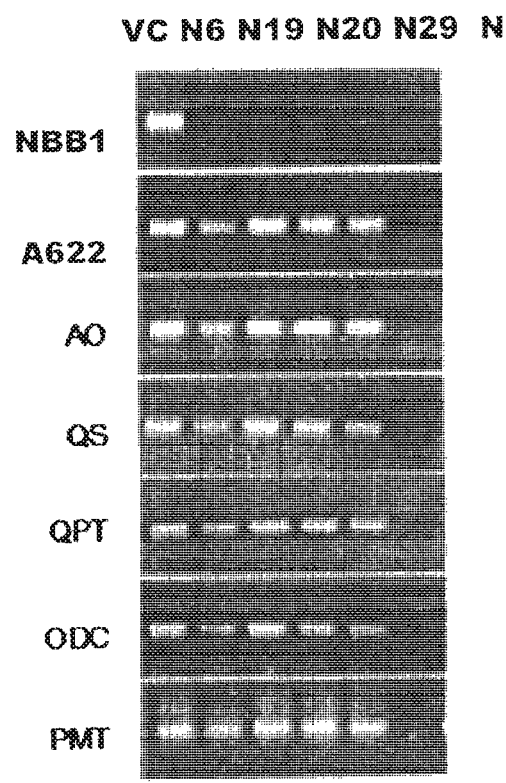
FIG. 14 depicts expression of NBB1, A622, and known enzymes involved in nicotine biosynthesis in NBB1-silenced and control hairy root lines.

Transgenic hairy roots carrying pHANNIBAL-NBB1 3' were grown in B5 medium for two weeks, and gene expression was analyzed by RT-PCR. NBB1 expression was specifically suppressed in four transgenic lines (See FIG. 14). NBB1 Expression of other genes for enzymes in the nicotine biosynthetic pathway was not affected.

The results demonstrate that reduced-nicotine accumulation results from reduced NBB1 expression, not a lack of expression of genes for known enzymes of the nicotine biosynthesis pathway.

Example 11: NBB1 Suppression in Transgenic Tobacco Plants

Two attB-NBB1 fragments were amplified by PCR from the NBB1 cDNA in pGEM-T vector using a primer set of NBB1-aatB1 and attB1 adapter, and a set of NBB1-attB2 and attB2 adapter.

Gene-specific primers:
(SEQ ID NOS 33-34)
NBB1-attB1
5' AAAAAGCAGGCTTCGAAGGAGATAGAACCATGGTTCCGCTCATAATT
CTGATCAGCTT NBB1-attB2
5' AGAAAGCTGGGTCTTCACTGCTATACTTGTGCTCTTGA Adapter primers:
(SEQ ID NOS 35-36)
attB1 adapter
5' GGGGACAAGTTTGTACAAAAAAGCAGGCT attB2 adapter
5' GGGGACCACTTTGTACAAGAAAGCTGGGT The PCR conditions used were those recommended by the manufacture. An entry clone pDONR221-NBB1-1 was created by BP recombination reactions between the attB-NBB1 PCR products and pDONR221 (Invitrogen).

The NBB1 ORF was transferred from the pDONR221-NBB1-1 vector to a GATEWAY binary vector pANDA 35HK which was designed to express a dsRNA with GUS partial fragment under the CaMV35S promoter (Dr. Ko Shimamoto, NAIST) by LR reaction. The resultant NBB1 RNAi vector is referred to as pANDA-NBB1full.

Figure 15:
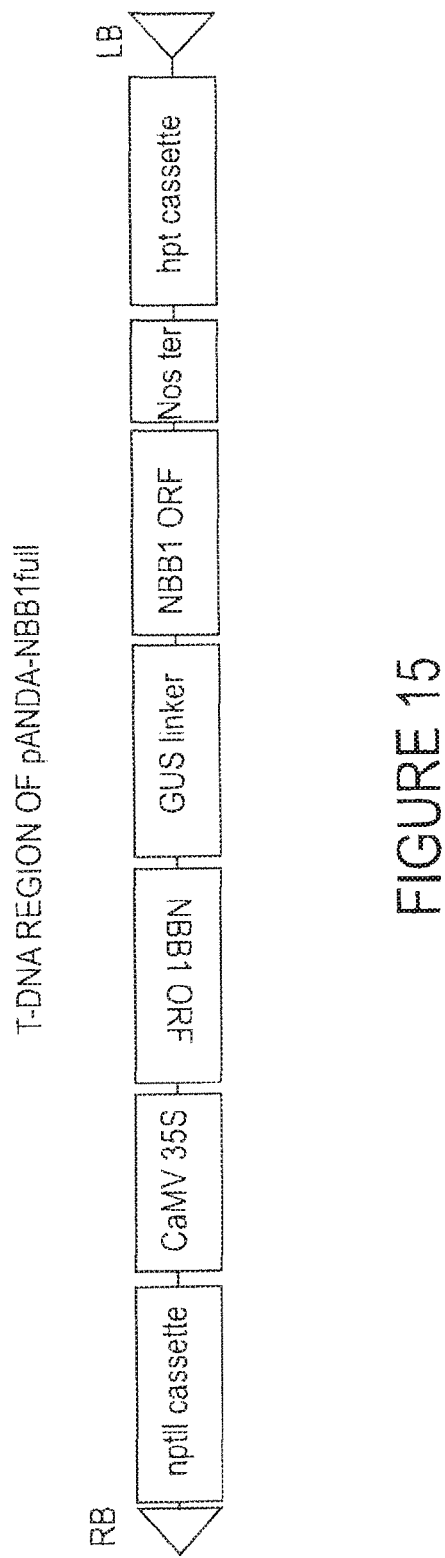
FIG. 15 depicts the T-DNA region of the NBB1 suppression vector pANDA-NBB1full.

The T-DNA of pANDA-NBB1full (See FIG. 15) contains an nptII selectable marker cassette, an NBB1 RNAi cassette in which the full length coding region of NBB1 is present in inverted repeats separated by a GUS linker, and an hpt selectable marker cassette.

The binary vector pANDA-NBB1 full was introduced to *A. tumefaciens* strain EHA105 by electroporation. *N. tabacum* cv. Petit Havana SR1 plants were transformed by *A. tumefaciens* using a leaf-disk method, basically as described by Kanegae et al., *Plant Physiol.* 105, 483-490 (1994). Hygromycin resistance (30 mg/L in MS medium) was used for selection. Transgenic plants were regenerated from the leaf discs as described and grown at 27° C. under continuous light in a growth chamber.

Figure 16:
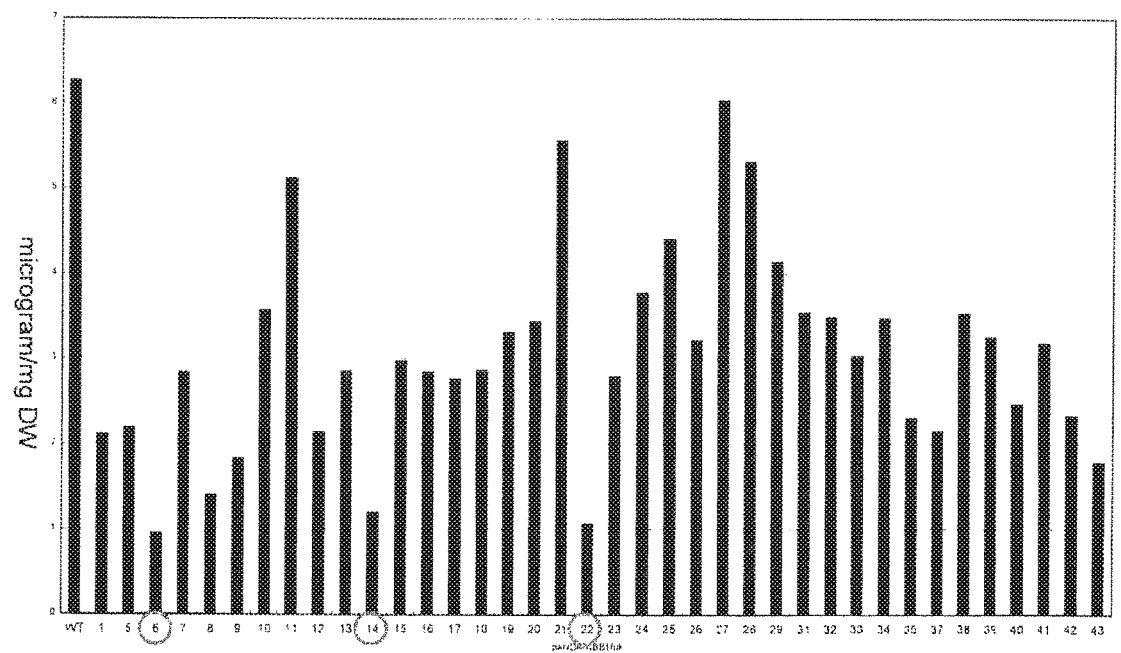
FIG. 16 depicts levels of nicotine in the leaves of *Nicotiana tabacum* plants from lines transformed with the NBB1 suppression vector pANDA-NBB1 full.

Leaf tissue was collected from TO generation plants grown for 36 days. Alkaloids were extracted, purified, and analyzed as described above. Levels of nicotine in the leaves of plants from lines transformed with the NBB1 suppression vector pANDA-NBB1full were reduced compared to wild type (See FIG. 16). Leaves of transgenic lines (#6, #14 and #22) contained levels of nicotine only about 16% of the level in leaves of wild type plants.

Sequence Listing

SEQ ID NO: 1
(A622 polynucleotide)
AAAAATCCGATTTAATTCCTAGTTTCTAGCCCCTCCACCTTAACCCGAAG
CTACTTTTTTTCTTCCCCTAGGAGTAAAATGGTTGTATCAGAGAAAGCA
AGATCTTAATAATTGGAGGCACAGGCTACATAGGAAAATACTTGGTGGAG
ACAAGTGCAAAATCTGGGCATCCAACTTTCGCTCTTATCAGAGAAAGCAC
ACTCAAAAACCCCGAGAAATCAAAACTCATCGACACATTCAAGAGTTATG
GGGTTACGCTACTTTTTGGAGATATATCCAATCAAGAGAGCTTACTCAAG
GCAATCAAGCAAGTTGATGTGGTGATTTCCACTGTCGGAGGACAGCAATT
TACTGATCAAGTGAACATCATCAAAGCAATTAAAGAAGCTGGAAATATCA
AGAGATTTCTTCCTTCAGAATTTGGATTTGATGTGGATCATGCTCGTGCA
ATTGAACCAGCTGCATCACTCTTCGCTCTAAAGGTAAGAATCAGGAGGAT
GATAGAGGCAGAAGGAATTCCATACACATATGTAATCTGCAATTGGTTTG
CAGATTTCTTCTTGCCCAACTTGGGGCAGTTAGAGGCCAAAACCCCTCCT
AGAGACAAAGTTGTCATTTTTGGCGATGGAAATCCCAAAGCAATATATGT
GAAGGAAGAAGACATAGCGACATACACTATCGAAGCAGTAGATGATCCAC
GGACATTGAATAAGACTCTTCACATGAGACCACCTGCCAATATTCTATCC
TTCAACGAGATAGTGTCCTTGTGGGAGGACAAAATTGGGAAGACCCTCGA
GAAGTTATATCTATCAGAGGAAGATATTCTCCAGATTGTACAAGAGGGAC
CTCTGCCATTAAGGACTAATTTGGCCATATGCCATTCAGTTTTTGTTAAT
GGAGATTCTGCAAACTTTGAGGTTCAGCCTCCTACAGGTGTCGAAGCCAC
TGAGCTATATCCAAAAGTGAAATACACAACCGTCGACGAGTTCTACAACA
AATTTGTCTAGTTTGTCGATATCAATCTGCGGTGACTCTATCAAACTTGT
TGTTTCTATGAATCTATTGAGTGTAATTGCAATAATTTTCGCTTCAGTGC
TTTTGCAACTGAAATGTACTAGCTAGTTGAACGCTAGCTAAATTCTTTAC
TGTTGTTTTCTATTTTTCGTCTTATTCCA SEQ ID NO: 2
(A622 polypeptide)
MVVSEKSKILIIGGTGYIGKYLVETSAKSGHPTFALIRESTLKNPEKSKL
IDTFKSYGVTLLFGDISNQESLLKAIKQVDVVISTVGGQQFTDQVNIIKA
IKEAGNIKRFLPSEFGFDVDHARAIEPAASLFALKVRIRRMIEAEGIPYT
YVICNWFADFFLPNLGQLEAKTPPRDKVVIFGDGNPKAIYVKEEDIATYT
IEAVDDPRTLNKTLHMRPPANILSFNEIVSLWEDKIGKTLEKLYLSEEDI
LQIVQEGPLPLRTNLAICHSVFVNGDSANFEVQPPTGVEATELYPKVKYT
TVDEFYNKFV SEQ ID NO: 3
(NBB1 polynucleotide)
ACGCGGGAGAAATACATACAACATGTTTCCGCTCATAATTCTGATCAGC
TTTTCACTTGCTTCCTTGTCTGAAACTGCTACTGGAGCTGTTACAAATCT
TTCAGCCTGCTTAATCAACCACAATGTCCATAACTTCTCTATTTACCCCA
CAAGTAGAAATTACTTTAACTTGCTCCACTTCTCCCTTCAAAATCTTCGC
TTTGCTGCACCTTTCATGCCGAAACCAACCTTCATTATCCTACCAAGCAG
TAAGGAGGAGCTCGTGAGCACCATTTTTTGTTGCAGAAAAGCATCTTATG
AAATCAGAGTAAGGTGCGGCGGACACAGTTACGAAGGAACTTCTTACGTT
TCCTTTGACGCTTCTCCATTCGTGATCGTTGACTTGATGAAATTAGACGA
CGTTTCAGTAGATTTGGATTCTGAAACAGCTTGGGCTCAGGGCGGCGCAA
CAATTGGCCAAATTTATTATGCCATTGCCAAGGTAAGTGACGTTCATGCA
TTTTCAGCAGGTTCGGGACCAACAGTAGGATCTGGAGGTCATATTTCAGG
TGGTGGATTTGGACTTTTATCTAGAAAATTCGGACTTGCTGCTGATAATG
TCGTTGATGCTCTTCTTATTGATGCTGATGGACGGTTATTAGACCGAAAA
GCCATGGGCGAAGACGTGTTTGGGCAATCAGAGGTGGCGGCGGTGGAAA
TTGGGGCATTGTTTATGCCTGGAAAATTCGATTACTCAAAGTGCCTAAAA
TCGTAACAACTTGTATGATCTATAGGCCTGGATCCAAACAATACGTGGCT
CAAATACTTGAGAAATGGCAAATAGTTACTCCAAATTTGGTCGATGATTT
TACTCTAGGAGTACTGCTGAGACCTGCAGATCTACCCGCGGATATGAAAT
ATGGTAATACTACTCCTATTGAAATATTTCCCCAATTCAATGCACTTTAT
TTGGGTCCAAAAACTGAAGTTCTTTCCATATCGAATGAGACATTTCCGGA
GCTAGGCGTTAAGAATGATGAGTGCAAGGAAATGACTTGGGTAGAGTCAG
CACTTTTCTTCTCCGAATTAGCTGACGTTAACGGGAACTCGACTGGTGAT
ATCTCCCGTCTGAAAGAACGTTACATGGACGGAAAAGGTTTTTTCAAAGG
CAAAACGGACTACGTGAAGAAGCCAGTTTCAATGGATGGGATGCTAACAT
TTCTTGTGGAACTCGAGAAAAACCCGAAAGGGATATCTTGTCTTTGATCT
TATGGCGGAGCCATGGACAAGATTAGTGATCAAGCTATTGCTTTCCCTCA
TAGAAAAGGTAACCTTTTCGCGATTCAGTATCTAGCACAGTGGAATGAAG
AGGACGATTACATGAGCGACGTTTACATGGAGTGGATAAGAGGATTTTAC
AATACAATGACGCCCTTTGTTTCAAGCTCGCCAAGGGGAGCTTATATCAA
CTACTTGGATATGGATCTTGGAGTGAATATGGTCGACGACTACTTATTGC
GAAATGCTAGTAGCAGTAGTCCTTCTTCCTCTGTTGATGCTGTGGAGAGA
GCTAGAGCGTGGGGTGAGATGTATTTCTTGCATAACTATGATAGGTTGGT
TAAAGCTAAGACACAAATTGATCCACTAAATGTTTTTCGACATGAACAGA
GTATTCCTCCTATGCTTGGTTCAACGCAAGAGCACAAGTATAGCAGTGAA
TGAGATTTAAAATGTACTACCTTGAGAGAGATTCCGTTGTTAGTTTTCC SEQ ID NO: 4
(NBB1 polypeptide)
MFPLIILISFSLASLSETATGAVTNLSACLINHNVHNFSIYPTSRNYFNL
LHFSLQNLRFAAPFMPKPTFIILPSSKEELVSTIFCCRKASYEIRVRCGG
HSYEGTSYVSFDASPFVIVDLMKLDDVSVDLDSETAWAQGGATIGQIYYA
IAKVSDVHAFSAGSGPTVGSGGHISGGGFGLLSRKFGLAADNVVDALLID
ADGRLLDRKAMGEDVFWAIRGGGGGNWGIVYAWKIRLLKVPKIVTTCMIY
RPGSKQYVAQILEKWQIVTPNLVDDFTLGVLLRPADLPADMKYGNTTPIE
IFPQFNALYLGPKTEVLSISNETFPELGVKNDECKEMTWVESALFFSELA
DVNGNSTGDISRLKERYMDGKGFFKGKTDYVKKPVSMDGMLTFLVELEKN
PKGYLVFDPYGGAMDKISDQATAFPHRKGNLFAIQYLAQWNEEDDYMSDV
YMEWIRGFYNTMTPFVSSSPRGAYINYLDMDLGVNMVDDYLLRNASSSSP
SSSVDAVERARAWGEMYFLHNYDRLVKAKTQIDPLNVFRHEQSIPPMLGS
TQEHKYSSE

What is claimed is:

1. A primer or probe pair capable of amplifying or detecting a nucleic acid molecule as set forth in SEQ ID NO: 3.

2. The primer or probe pair of claim 1, wherein the probe pair comprises isolated nucleic acid molecules comprising:
   (a) a first nucleic acid molecule comprising 15-1680 contiguous nucleotides of SEQ ID NO: 3; and
   (b) and a second nucleic acid molecule comprising 15-1680 contiguous nucleotides of SEQ ID NO: 3,
   wherein the first and second nucleic acid molecules function together as primers or probes for a nucleic acid sequence as set forth in SEQ ID NO: 3.

3. A method for identifying a tobacco plant comprising a mutant allele of the polynucleotide sequence as set forth in SEQ ID NO: 3, comprising:
   (a) obtaining a nucleic acid sample from one or more tobacco plants; and
   (b) contacting the sample with a nucleic acid primer comprising 15-1680 contiguous nucleotides of SEQ ID NO: 3 or its complement; and
   (c) identifying a sample having a nucleic acid sequence comprising the mutant allele of the polynucleotide as set forth in SEQ ID NO: 3.

4. The method of claim 3, wherein the identifying method step comprises detecting formation of a heteroduplex, wherein the heteroduplex detects the mutant allele of the nucleic acid sequence as set forth in SEQ ID NO: 3.

5. A method for identifying a tobacco plant with reduced expression of the polynucleotide sequence as set forth in SEQ ID NO: 3, comprising:
   (a) measuring expression of the polynucleotide sequence as set forth in SEQ ID NO: 3 in a population of tobacco plants; and
   (b) selecting a tobacco plant with reduced expression of the polynucleotide sequence as set forth in SEQ ID NO: 3 relative to wild-type levels of expression of the polynucleotide sequence as set forth in SEQ ID NO: 3.

6. The method of claim 5, wherein the measuring of expression of the polynucleotide sequence as set forth in SEQ ID NO: 3 uses a primer or probe pair capable of amplifying or detecting a nucleic acid molecule as set forth in SEQ ID NO: 3.

7. A tobacco plant identified with the method of claim 3, wherein the plant comprises the mutant allele of the polynucleotide sequence as set forth in SEQ ID NO: 3 and has reduced expression of the polynucleotide sequence as set forth in SEQ ID NO: 3 as compared to wild-type levels of expression of the polynucleotide sequence as set forth in SEQ ID NO: 3.

8. A product produced from the tobacco plant of claim 7, wherein the product comprises the mutant allele of the polynucleotide sequence as set forth in SEQ ID NO: 3.

9. The product of claim 8, wherein the product is selected from the group consisting of smoking cessation products, cigarettes, cigarette tobacco, cigars, cigar tobacco, snus, pipe tobacco and chewing tobacco.

10. The product of claim 8, wherein the product is selected from the group consisting of a food product, food ingredient, feed product, feed ingredient, nutritional supplement, and biofuels.

* * * * *